United States Patent
Perrine

US008242172B2

(10) Patent No.: US 8,242,172 B2
(45) Date of Patent: *Aug. 14, 2012

(54) 2,2-DIMETHYLBUTYRIC ACID ORAL PHARMACEUTICAL COMPOSITIONS

(75) Inventor: Susan P. Perrine, Weston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/836,344

(22) Filed: Jul. 14, 2010

(65) Prior Publication Data

US 2010/0280113 A1 Nov. 4, 2010

Related U.S. Application Data

(60) Continuation of application No. 11/827,362, filed on Jul. 11, 2007, now abandoned, which is a division of application No. 10/185,745, filed on Jul. 1, 2002, now Pat. No. 7,265,153, which is a division of application No. 09/248,260, filed on Feb. 11, 1999, now abandoned.

(60) Provisional application No. 60/074,304, filed on Feb. 11, 1998.

(51) Int. Cl.
*A61K 31/225* (2006.01)
*A61K 31/22* (2006.01)
*A61K 31/19* (2006.01)

(52) U.S. Cl. .................. 514/547; 514/549; 514/557

(58) Field of Classification Search .............. 514/547, 514/549, 557, 577
See application file for complete search history.

(56) References Cited

U.S. PATENT DOCUMENTS

| 3,471,513 A | 10/1969 | Chinn et al. |
| 3,904,612 A | 9/1975 | Nagasawa et al. |
| 4,008,323 A | 2/1977 | Cousse et al. |
| 4,011,336 A | 3/1977 | Amann et al. |
| 4,026,896 A | 5/1977 | Harita et al. |
| 4,031,243 A | 6/1977 | Aparicio et al. |
| 4,058,558 A | 11/1977 | Cousse et al. |
| 4,131,617 A | 12/1978 | Esanu |
| 4,176,193 A | 11/1979 | Esanu |
| 4,234,599 A | 11/1980 | Van Scott et al. |
| 4,613,616 A | 9/1986 | Winston et al. |
| 4,671,901 A | 6/1987 | Green |
| 4,699,926 A | 10/1987 | Abraham et al. |
| 4,704,402 A | 11/1987 | Abraham et al. |
| 4,723,958 A | 2/1988 | Pope et al. |
| 4,731,381 A | 3/1988 | Abraham et al. |
| 4,732,914 A | 3/1988 | Morton, Jr. |
| 4,735,967 A | 4/1988 | Neesby |
| 4,747,825 A | 5/1988 | Linkie et al. |
| 4,751,244 A | 6/1988 | Abraham et al. |
| 4,820,711 A | 4/1989 | Pearlman |
| 4,822,821 A | 4/1989 | Perrine |
| 4,849,426 A | 7/1989 | Pearlman |
| 4,851,229 A | 7/1989 | Magruder et al. |
| 4,853,388 A | 8/1989 | Pearlman |
| 4,880,624 A | 11/1989 | Metcalf et al. |
| 4,894,364 A | 1/1990 | Greer |
| 4,925,873 A | 5/1990 | Friedhoff et al. |
| 4,952,560 A | 8/1990 | Kigasawa et al. |
| 4,958,592 A | 9/1990 | Anthony et al. |
| 4,965,251 A | 10/1990 | Stamatoyannopoulos |
| 4,997,815 A | 3/1991 | Perrine et al. |
| 5,023,251 A | 6/1991 | Sattler et al. |
| 5,025,029 A | 6/1991 | Perrine |
| 5,032,507 A | 7/1991 | Yu et al. |
| 5,039,703 A | 8/1991 | Breuer |
| 5,081,124 A | 1/1992 | Hughes |
| 5,100,647 A | 3/1992 | Agus et al. |
| 5,137,734 A | 8/1992 | Spiegeman et al. |
| 5,185,436 A | 2/1993 | Villa et al. |
| 5,199,942 A | 4/1993 | Gillis |
| 5,208,333 A | 5/1993 | Paul et al. |
| 5,216,004 A | 6/1993 | Perrine |
| 5,258,367 A | 11/1993 | Bazer et al. |
| 5,270,458 A | 12/1993 | Lemischka |
| 5,366,996 A | 11/1994 | Elford |
| 5,378,716 A | 1/1995 | Hamanaka et al. |
| 5,403,590 A | 4/1995 | Forse |
| 5,403,867 A | 4/1995 | Okumura et al. |
| 5,468,731 A | 11/1995 | Matsuo et al. |
| 5,635,532 A | 6/1997 | Samid |
| 5,654,333 A | 8/1997 | Samid |

(Continued)

FOREIGN PATENT DOCUMENTS

CA         1209037 A         8/1986

(Continued)

OTHER PUBLICATIONS

Osato, et al. Epstein-Barr virus and gastric carcinoma. Semin Cancer Biol. 1996;7:175-182.
Pace, et al. Short-chain fatty acid derivatives induce fetal globin expression and erythropoiesis in vivo. Blood. Dec. 15, 2002;100(13):4640-8.
Pagano. Epstein-Barr virus: the first human tumor virus and its role in cancer. Proc Assoc Am Physicians. 1999;111:573-580.
Parise, et al. Liquid chromatography-mass spectrometric assay for quantitation of the short-chain fatty acid, 2,2-dimethylbutyrate (NSC 741804), in rat plasma. J Chromatogr B Analyt Technol Biomed Life Sci. Feb. 1, 2008;862(1-2):168-74.

(Continued)

*Primary Examiner* — Raymond Henley, III
(74) *Attorney, Agent, or Firm* — Nixon Peabody LLP

(57) ABSTRACT

The invention is directed to novel pharmaceutical compositions comprising chemicals agents that are useful in the treatment and prevention of cystic fibrosis and the prevention of signs and symptoms of this disease. These pharmaceutical compositions are surprisingly successful in the treatment disorders related to cystic fibrosis including disorders of blood production. Many of these compositions of the invention are even more effective when administered to a patient in pulses. Pulse therapy is not a form of discontinuous administration of the same amount of a composition over time, but comprises administration of the same dose of the composition at a reduced frequency or administration of reduced doses.

5 Claims, No Drawings

U.S. PATENT DOCUMENTS

| | | |
|---|---|---|
| 5,661,179 A | 8/1997 | Samid |
| 5,674,898 A | 10/1997 | Cheng et al. |
| 5,674,912 A | 10/1997 | Martin |
| 5,679,707 A | 10/1997 | Okumura et al. |
| 5,710,178 A | 1/1998 | Samid |
| 5,750,571 A | 5/1998 | Cheng et al. |
| 5,780,451 A | 7/1998 | DeMichele et al. |
| 5,843,994 A | 12/1998 | Samid |
| 5,846,528 A | 12/1998 | Podsakoff et al. |
| 5,852,056 A | 12/1998 | Samid |
| 5,858,365 A | 1/1999 | Faller et al. |
| 5,883,123 A | 3/1999 | Tung et al. |
| 5,912,269 A | 6/1999 | Tung et al. |
| 5,932,545 A | 8/1999 | Henkin et al. |
| 5,939,456 A | 8/1999 | Perrine |
| 5,945,407 A | 8/1999 | Bemis et al. |
| 5,952,314 A | 9/1999 | DeMichele et al. |
| 6,011,000 A | 1/2000 | Perrine et al. |
| 6,030,961 A | 2/2000 | Nudelman et al. |
| 6,043,389 A | 3/2000 | Nudelman et al. |
| 6,197,743 B1 | 3/2001 | Faller |
| 6,231,880 B1 | 5/2001 | Perrine |
| 6,403,647 B1 | 6/2002 | Perrine |
| 6,451,334 B2 | 9/2002 | Perrine |
| 6,677,302 B2 | 1/2004 | Faller |
| 7,192,715 B2 | 3/2007 | Harley et al. |
| 7,265,153 B2 | 9/2007 | Faller et al. |
| 2001/0009922 A1 | 7/2001 | Faller |
| 2001/0027215 A1 | 10/2001 | Perrine |
| 2003/0018069 A1 | 1/2003 | Faller et al. |
| 2003/0077297 A1 | 4/2003 | Chen et al. |
| 2006/0074046 A1 | 4/2006 | Redkar et al. |
| 2007/0232528 A1 | 10/2007 | Franke |
| 2008/0027136 A1 | 1/2008 | Faller et al. |
| 2008/0057086 A1 | 3/2008 | Etter |
| 2008/0175849 A1 | 7/2008 | Smith et al. |
| 2008/0254026 A1 | 10/2008 | Long et al. |
| 2009/0082444 A1 | 3/2009 | Perrine |
| 2009/0130134 A1 | 5/2009 | Pancre et al. |

FOREIGN PATENT DOCUMENTS

| | | |
|---|---|---|
| CA | 2303268 A1 | 4/1995 |
| CA | 2173976 A1 | 2/2008 |
| EP | 0069659 A1 | 1/1983 |
| EP | 0224599 A1 | 6/1987 |
| EP | 0320726 A2 | 6/1989 |
| EP | 0324574 A2 | 7/1989 |
| EP | 0350287 A2 | 1/1990 |
| EP | 371789 A2 | 6/1990 |
| EP | 0320726 A3 | 8/1990 |
| EP | 0324574 A3 | 12/1990 |
| EP | 0546261 A2 | 6/1993 |
| EP | 0546261 A3 | 8/1993 |
| EP | 0617966 A1 | 10/1994 |
| GB | 2126082 A | 3/1984 |
| JP | 50-89335 | 7/1975 |
| JP | 61-180740 A | 8/1986 |
| WO | WO 90/11071 A1 | 10/1990 |
| WO | WO 91/01719 A1 | 2/1991 |
| WO | WO 92/03155 A1 | 3/1992 |
| WO | 92/04913 | 4/1992 |
| WO | WO 93/07866 A2 | 4/1993 |
| WO | 93/18761 | 9/1993 |
| WO | 94/04671 | 3/1994 |
| WO | WO 94/04671 A1 | 3/1994 |
| WO | WO 95/10271 A1 | 4/1995 |
| WO | WO 95/10271 A2 | 4/1995 |
| WO | 95/11699 | 5/1995 |
| WO | WO 95/10271 A3 | 6/1995 |
| WO | WO 96/02244 A1 | 2/1996 |
| WO | 96/27369 | 9/1996 |
| WO | WO 96/27369 A3 | 11/1996 |
| WO | 97/04761 | 2/1997 |
| WO | WO 97/04761 A1 | 2/1997 |
| WO | 98/04290 | 2/1998 |
| WO | WO 98/04290 A3 | 8/1998 |
| WO | 98/40078 | 9/1998 |
| WO | WO 98/40078 A1 | 9/1998 |
| WO | 98/56370 | 12/1998 |
| WO | WO 98/56370 A2 | 12/1998 |
| WO | WO 98/56370 A3 | 4/1999 |
| WO | WO 2007/133653 A2 | 11/2007 |

OTHER PUBLICATIONS

Perrine, et al. A phase 1,2 trial of arginine butyrate and ganciclovir in patients with Epstein-Barr virus-associated lymphoid malignancies. Blood. 2007;109(6):2571-2578.

Perrine, et al. Benign sickle-cell anaemia. Lancet. Dec. 2, 1972:1163-67.

Perrine, et al. Butyrate infusions in the ovine fetus delay the biologic clock for globin gene switching. Proc. Natl. Acad. Sci. USA. 1988;85:8540-8542.

Perrine, et al. Butyrate-induced reactivation of the fetal globin genes: a molecular treatment for the beta-hemoglobinopathies. Experientia. Feb. 15, 1993;49(2):133-7.

Perrine, et al. HQK-1001 has additive HbF-inducing activity in combination with hydroxyurea & decitabine. Slides presented at ASH Annual Meeting and Exposition. Dec. 2009.

Perrine, et al. Induction of fetal globin in b-thalassemia: cellular obstacles and molecular progress. Ann N.Y. Acad. Sci. 2005;1054:257-265.

Perrine, et al. Natural history of sickle cell anemia in Saudi Arabs. Ann Intern Med. 1978;88(1):1-6.

Perrine, et al. Phase 1 clinical testing of HQK-1001, a novel oral fetal globin gene inducer. Abstract from ASH Annual Meeting and Exposition. Dec. 2008.

Perrine, et al. Phase 1 clinical testing of HQK-1001, a novel oral fetal globin stimulant. Slides presented at ASH Annual Meeting and Exposition. Dec. 2008.

Perrine, et al. RH-Activin increases erythroid progenitor growth and Hb F in childhood red cell failure syndromes and hemoglobinopathies. Blood. 1989;74(7), Suppl. 1: Abstract p. 114a.

Perrine. Fetal globin induction—can it cure beta thalassemia? Hematology. 2005:38-44.

Planchon, et al. New stable butyrate derivatives alter proliferation and differentiation in human mammary cells. Int J Cancer. May 30, 1991;48(3):443-9.

Platt, et al. Pain in sickle cell disease. N Engl J Med. Jul. 4, 1991;325(1):11-16.

Pootrakul, et al. A correlation of erythrokinetics, ineffective erythropoiesis, and erythrod precursor apoptosis in Thai patients with thalassemia. Blood. Oct. 1, 2000;96(7):2606-12.

Powars, et al. Is there a threshold level of fetal hemoglobin that ameliorates morbidity in sickle cell anemia? Blood. Apr. 1984;63(4):921-926.

Rachmilewitz, et al. The role of recombinant human erythropoietin in the treatment of thalassemia. Ann N.Y Acad Sci. vol. 850 Issue Cooley's Anemia: Seventh Symposium. Feb. 7, 2006:129-138.

Reynolds. Cinamic Acid (Ban) The Extra Pharmacopoeia, 29th edition, 1989:1359-1360.

Rickinson, et al. Epstein-Barr virus. In Fields Virology, vol. 2, 3rd Ed., B.N. Fields, D.M. Knipe, and P.M. Howley, eds. Lippincott-Raven, Philadelphia. 1996:2397-2446.

Rowe, et al. Colonic short-chain fatty acids: fuel from the lumen? Gastroenterology. Jul. 1992;103(1):336-8.

Rubenstein, et al. A pilot clinical trial of oral sodium 4-phenylbutyrate (Buphenyl) In DELTAF508-homozygous cystic fibrosis patients: Partial restoration of nasal epithelial CFTR function. American Journal of Respiratory and Critical Care Medicine. Feb. 1998;157(2):484-490.

Rubenstein, et al. In vitro pharmacologic restoration of CFTR-mediated chloride transport with sodium 4-phenylbutyrate in cystic fibrosis epithelial cells containing delta F508-CFTR. J Clin Invest. Nov. 15, 1997;100(10):2457-2465.

Rund, et al. B-Thalassemia. N. Engl J Med. Sep. 15, 2005;353(11):1135-46.

Sadaie, et al. Induction of developmentally programmed cell death and activation of HIV by sodium butyrate. Virology. 1994;202:513-518.

Scherr, et al. School contact among persons with Hodgkin's disease. Am J. Epidemiol. 1984;120:29-38.

Sher, et al. Rapid healing of chronic leg ulcers during arginine butyrate therapy in patients with sickle cell disease and thalassemia. Blood. Oct. 1, 1994;84(7):2378-80.

Shibata, et al. Epstein-Barr virus-associated non-Hodgkin's lymphoma in patients infected with the human immunodeficiency virus. Blood. 1993;81:2101-2109.

Singer, et al. Fetal haemoglobin augmentation in E/β0 thalassaemia: clinical and haematological outcome. Br J Haematol. 2005;131:378-88.

Speck, et al. Infection of breast epithelial cells with Epstein-Barr virus via cell-to-cell contact. J Nat Cancer Inst. 2000;92:1849-1851.

Sripichai, et al. A scoring system for the classification of β-thalassemia/Hb E disease severity. Am J Hematol. Jun. 2008;83(6):482-4.

Steinberg, et al. Effect of hydroxyurea on mortality and morbidity in adult sickle cell anemia. JAMA. Apr. 2, 2003;289(13):1645-52.

Steinberg, et al. Fetal hemoglobin in sickle cell anemia: determinants of response to hydroxyurea. Blood. Feb. 1, 1997;89(3):1078-1088.

Steinberg, et al. Pharmacologic modulation of fetal hemoglobin. Medicine. 2001;80(5):328-44.

Steinberg. Predicting clinical severity in sickle cell anaemia. British Journal of Haematology. 2005;129(4):465-81.

Su, et al. Aggressive peripheral T-cell lymphomas containing Epstein-Barr viral DNA: A clinicopathologic and molecular analysis. Blood. 1991;77:799-808.

Swinnen. Overview of posttransplant B-cell lymphoproliferative disorders. Semin Oncol. 1999;26:21-25.

Tang, et al. Memory of butyrate induction by the moloney murine sarcoma virus enhancer-promoter element. Biochem and Biophys Res. Comm 1992;189(1):141-147.

Testa. Apoptotic mechanisms in the control of erythropoiesis. Leukemia. 2004;18:1176-99.

The Merck Index of Chemicals and Drugs, 7th edition, 1960:434-435.

Toussirot, et al. Epstein-Barr virus in autoimmune diseases. Best Practice & Research Clinical Rheumatology. 2008;22(5):883-896.

Vichinsky, et al. Changes in the epidemiology of thalassemia in north america: a new minority disease. Pediatrics. Dec. 2005;116(6):e818-e25.

Vichinsky. Changing patterns of thalassemia worldwide. Annals of the N.Y. Academy of Science. 2005;1054:18-24.

Vichinsky. Hemoglobin E Syndromes. Hematology/The Education Program of the American Society of Hematology. 2007:79-83.

Vile, et al. Systemic gene therapy of murine melanoma using tissue specific expression of the HSVtk gene involves an immune component. Cancer Res. Dec. 1, 1994;54(23):6228-34.

Walsh, et al. Combination of drug and gene delivery by gelatin nanospheres for the treatment of cystic fibrosis. Proceedings of the International Symposium on Controlled Release of Bioactive Materials, U.S., Deerfield, IL, controlled Release Soc., vol. SYMP, 24, Jun. 15, 1997:75-76.

Watkins, et al. Choleretic effect of structural analogs of valproic acid in the rat. Res Commun Chem Pathol Pharmacol. Mar. 1983;39(3):355-66.

Weatherall, et al. A model for the persistence or reactivation of fetal haemoglobin production. The Lancet. Sep. 25, 1976;308(7987):660-63.

Weiss, et al. Detection of Epstein-Barr virus in Reed-Sternberg cells of Hodgkin's disease. N. Engl J Med. 1989;320(8):502-506.

Weiss, et al. Epstein-Barr viral DNA in tissues of Hodgkin's disease. Am J Pathol. 1987;129:86-91.

Weiss, et al. Epstein-Barr virus and Hodgkin's disease. A correlative in situ hybridization and polymerase chain reaction study. Am J Pathol. 1991;139:1259-1265.

Winichagoon, et al. β-Thalassemia in Thailand. Annals of the New York Academy of Sciences. 1990;612:31-42.

U.S. Appl. No. 12/834,720, filed Jul. 12, 2010, Berenson et al.

U.S. Appl. No. 12/836,344, filed Jul. 14, 2010, Faller.

Angastiniotis, et al. Global epidemiology of hemoglobin disorders. Ann N Y Acad Sci—Issue Cooley's Anemia: Seventh Symposium. Feb. 7, 2006;850:251-269. (Published Online).

Antoni, et al. NF-.kappa. B-Dependent and -Independent Pathways of HIV Activation in a Chronically Infected T Cell Line. Virology. 1994;202:684-694.

Armstrong, et al. Criteria for the definition of Epstein-Barr virus association in Hodgkin's disease. Leukemia. 1992;6:869-874.

Atweh, et al. Pharmacological induction of fetal hemoglobin in sickle cell disease and b-Thalassemia. Seminars in Hematology. 2001;38(4):367-373.

Atweh, et al. Sustained induction of fetal hemoglobin by pulsed butyrate therapy in sickle cell disease. Blood. 1999;93(6):1790-1797.

Barbul, et al. Arginine enhances wound healing and lymphocyte immune responses in humans. Surgery. Aug. 1990;108(2):331-6; discussion 336-7.

Basson, et al. Butyrate-induced enterocyte differentiation and mucosal wound healing. Gastroenterology. 1993; 104(4) supp.:A235.

Berkovitch, et al. Pharmacokinetics of arginine butyrate in patients with hemoglobinopathy. Environ Tox and Pharm. 1996;2(4):403-405.

Bingham. Patty's Toxicology. John Wiley and Sons, Incorporated. Jan. 1, 2001;5:707-711.

Birgens, et al. The thalassaemia syndromes. Scand J Clin Lab Invest. 2007; 67(1):11-26.

Blau, et al. Fetal hemoglobin induction with butyric acid: efficacy and toxicity. Blood. Jan. 15, 1993;81(2):529-37.

Bohacek, et al. Identification of novel small-molecule inducers of fetal hemoglobin using pharmacophore and 'PSEUDO' receptor models. Chem Biol and Drug Design. 2006;67(5):318-328.

Bohan, et al. Mutational analysis of sodium butyrate inducible elements in the human immunodeficiency virus type 1 long terminal repeat. Virology. 1989;172:573-583.

Bohan, et al. Sodium butyrate activates human immunodeficiency virus long terminal repeat—directed expression. Biochem and Biophys. Res. Comm 1987;148(3):899-905.

Bokiri, et al. Swine experiment with a feed containing sodium-n-butyrate. Chemical Abstracts. 1990;112(3):438.

Bonnet, et al. Detection of Epstein-Barr virus in invasive breast cancers. J Nat Cancer Inst. 1999;91(16):1376-1381.

Boosalis, et al. Short-chain fatty acid derivatives stimulate cell proliferation and induce STAT-5 activation. Blood. May 15, 2001;97(10):3259-67.

Borgna-Pignatti, et al. Modern treatment of thalassaemia intermedia. Br J Haematol. 2007;138:291-304.

Borgna-Pignatti, et al. Survival and complications in thalassemia. Ann N Y Acad Sci—Issue Cooley's Anemia: Eighth Symposium. Jan. 6, 2005;1054:40-47. (Published Online).

Bourantas, et al. Administration of high dose of recombinant human erythropoietin to patients with βthalassemia intermedia: a preliminary trial. Eur J Haematol. 1997;58:22-25.

Bourgeade, et al. Effect of sodium butyrate on the antiviral and anticellular action of interferon in normal and MSV-transformed cells. Int J Cancer. Sep. 15, 1979;24(3):314-8.

Briz, et al. Epstein-Barr virus associated B-cell lymphoma after autologous bone marrow transplantation for T-cell acute lymphoblastic leukaemia. Br J Haematol. 1997;98:485-487.

Brooks, et al. Epstein-Barr virus and lymphomas. Cancer Surv. 1999;33:99-123.

Brousset, et al. Detection of Epstein-Barr virus messenger RNA in Reed-Sternberg cells of Hodgkin's disease by in situ hybridization with biotinylated probes on specially processed modified acetone methyl benzoate xylene (ModAMeX) sections. Blood. 1991;77:1781-1786.

Bunn. Mechanisms of disease—pathogenesis and treatment of sickle cell disease. N Engl J Med. Sep. 11, 1997;337:762-769.

Burkitt. A sarcoma involving the jaws in African children. C.A. Cancer J. Clin. 1992: 349-355.

Caruso, et al. Regression of established macroscopic liver metastases after in situ transduction of a suicide gene. Proc Natl Acad Sci U S A. Aug. 1, 1993;90(15):7024-8.

Castaneda, et al. Enhancement of growth and survival and alterations in Bcl-family proteins in β-thalassemic erythroid progenitors by novel short-chain fatty acid derivatives. Blood Cells Mol. Dis. 2005;35(2):217-26.

Chang, et al. An analysis of fetal hemoglobin variation in sickle cell disease: the relative contributions of the X-linked factor, beta-globin haplotypes, alpha-globin gene number, gender, and age. Blood. Feb. 15, 1995;85(4):1111-1117.

Cheng, et al. Functional activation of the cystic fibrosis trafficking mutant .DELTA.F508-CFTR by expression. Am. J. Physiol. 1995;268:L615-24.

Chu, et al. In situ detection of Epstein-Barr virus in breast cancer. Cancer Lett. 1998;124:53-57.

Coates, et al. Persistence of Epstein-Barr virus in Reed-Sternberg cells throughout the course of Hodgkin's disease. J Pathol. 1991;164:291-291.

Cohen, et al. Thalassemia. Hematology-American Society of Hematology Education Program Book. 2004:14-34.

Colombo. Natural history and pathogenesis of hepatitis C virus related hepatocellular carcinoma. Journal of Hepatology. 1999;31:(1):25-30. Suppl.

Curtis, et al. Risk of lymphoproliferative disorders after bone marrow transplantation: A multi-institutional study. Blood. 1999;94:2208-2216.

Dakshinamurty, et al. Ternary liquid equilibrium systems ethanol-water-methyl isobutyl carbinol and acetic acid-water-ethyl butyrate. J. Chem. Eng. Data. 1972;17(3):379-383.

Dantchev,et al. Behavior of certain Pyrimidine compounds of fumeric acid, and of malic acid with regard to the protection of red blood cells of the rabbit intoxicated with phenylhydrazine. Acad. Sci. Hebd. Sceances Acad. Sci. D. Mar. 1967;264(11):1467-1470. (in French with English abstract).

De Bruin, et al. Detection of Epstein-Barr virus nucleic acid sequences and protein in nodal T-cell lymphomas: relation between latent membrane protein I positively and clinical course. Histopathology. 1993;23:509-518.

De Bruin, et al. Presence of Epstein-Barr virus in extranodal T-cell lymphomas: differences in relation to site. Blood. 1994;83(10):1612-1618.

Dimaio, et al. Directed enzyme pro-drug gene therapy for pancreatic cancer in vivo. Surgery. Aug. 1994;116(2):205-13.

Donaldson, et al. Cytotoxicity of the anticancer agents cisplatin and taxol during cell proliferation and the cell cycle. Int J Cancer. Jun. 15, 1994;57(6):847-55.

Douillard, et al. Phase I trial of interleukin 2 (IL2) and arginine butyrate (ArgB) in metastatic colorectal cancer. Proc. Am. Assn. for Cancer Research. 1998;39:606. (Abstract only).

Dover, et al. Fetal hemoglobin levels in sickle cell disease and normal individuals are partially controlled by an x-linked gene located at Xp22.2. Blood. 1992;80(3):816-824.

El Rassi, et al. Beta-thalassemia intermedia: an overview. Pediat Ann. May 2008;37(5):322-8.

El-Nawawy, et al. Organic pesticides. II. (Arylthio) acetic acids, (arylenedithio) diacetic acids, and several of their S-alkylisothiuronium salts. Alexandria J. Agr. Res. 1970;16(2):173-184, (Abstract only).

European search report dated Jun. 16, 2005 for Application No. EP 94930734.2.

European search report dated Jun. 9, 2009 for Application No. EP 6021311.3.

Evans, et al. A population-based case-control study of EBV and other viral antibodies among persons with Hodgkin's disease and their siblings. Int J Cancer. 1984;34:149-149.

Faller, et al. Arginine butyrate-induced susceptibility to ganciclovir in an Epstein-Barr Virus (EBV) associated lymphona. Am. Soc. of Hematology [Blood]. 1995;86(10)(1):342a.

Faller, et al. Arginine Butyrate-induced susceptibility to ganciclovir in Epstein-Barr virus (EBV)-associated lymphomas. Proceedings of the American Association for Cancer Research. 1996;37:411-412.

Faller, et al. Phase I/II trial of arginne butyrate to induce viral TK gene expression in Epstein-Barr Virus (EBV)-associated lymphomas. Proc. Am. Assn. for Cancer Research. Mar. 2000;41:544. (Abstract only).

Franco, et al. The effect of fetal hemoglobin on the survival characteristics of sickle cells. Blood. Aug. 1, 2006;108(3):1073-1076.

Franke, et al. [Experiences with alpha-aminoisobutyric acid in the treatment of wounds.] Zentralbl Chir. 1954;79(18):769-76.

Fucharoen, et al. Clinical and hematologic aspects of hemoglobin E [beta]—thalassemia. Curr Opin Hematol. Mar. 2000;7(2):106-112.

Fucharoen, et al. Hemoglobinopathies in Southeast Asia. Hemoglobin. 1987;11(1):65-88.

Fucharoen, et al. Thalassemia in SouthEast Asia: problems and strategy for prevention and control. Southeast Asian J Trop Med Public Health. Dec. 1992;23(4):647-55.

Fucharoen, et al. α- and β-Thalassemia in Thailand. Ann N Y Acad Sci. Jun. 30, 1998;850:412-4.

Gilbert, et al. A phase I dose escalation and bioavailability study of oral sodium phenylbutyrate in patients with refractory solid tumor malignancies. Clin Cancer Res. Aug. 2001;7(8):2292-300.

Gladwin, et al. Pulmonary hypertension as a risk factor for death in patients with sickle cell disease. N Engl J Med. Feb. 26, 2004;350(9):886-895.

Gladwin. Unraveling the hemolytic subphenotype of sickle cell disease. Blood. Nov. 1, 2005;106(9):2925-2926.

Glaser, et al. Epstein-Barr virus-associated Hodgkin's disease: epidemiologic characteristics in international data. Int J Cancer. 1997;70(4):375-382.

Golub, et al. Induction of dormant HIV-1 by sodium butyrate: involvement of the TATA box in the activation of the HIV-1 promoter. AIDS. 1991;5(6):663-668.

Gredmark, et al. Active cytomegalovirus replication in patients with coronary disease. Scand Cardiovasc J. Aug. 2007;41(4):230-4.

Greenspan, et al. Replication of Epstein-Barr virus within the epithelial cells of oral "hairy" leukoplakia, an AIDS-associated lesion. N Engl J Med. 1985;313:1564-1571.

Gross, et al. B cell lymphoproliferative disorders following hematopoietic stem cell transplantation. Risk factors, treatment and outcome. Bone Marrow Transplant. 1999;23:251-258.

Grufferman, et al. Hodgkin's disease in siblings. N Engl J Med. 1977;296:248-250.

Gum, et al. Effects of sodium butyrate on human colonic adenocarcinoma cells. The Journal of Biological Chemistry. Jan. 25, 1987;262(3):1092-1097.

Hahn, et al. Therapeutic outcome of Epstein-Barr virus positive T/NK cell lymphoma in the upper aerodigestive tract. Yonsei Med J. 2002;43:175-182.

Hanto, et al. Epstein-Barr virus-induced polyclonal and monoclonal B-cell lymphoproliferative diseases occurring after renal transplantation. Ann Surg. 1983;198:356-369.

Harabuchi, et al. Epstein-Barr virus in nasal T-cell lymphomas in patients with lethal midline granuloma. Lancet. 1990;335:128-130.

Henle, et al. Epstein-Barr virus and human malignancies. Cancer. 1974;34: 1386-1374.

Henle, et al. Relation of Burkitt's tumor-associated herpes-type virus to infectious mononucleosis. Proc Natl Acad Sci USA. Microbiology, 1968;58:94-101.

Herbst, et al. Epstein-Barr virus latent membrane protein expression in Hodgkin and Reed-Sternberg cells. Proc Natl Acad Sci USA. 1991;88:4766-4770.

Ho, et al. Presence of Epstein-Barr virus DNA in nasal lymphomas. Hematol Oncol. 1990;8:271-281.

European office action dated Aug. 11, 2010 for Application No. 6021311.3.

International search report and written opinion dated Dec. 15, 2010 for PCT Application No. US10/50191.

EP 10184726 Search Report mailed Jan. 20, 2011.

PCT/US10/59584 Search Report and Written Opinion mailed Feb. 11, 2011.

Hsu, et al. Epstein-Barr virus-associated malignancies: epidemiologic patterns and etiologic implications. Crit Rev Oncol Hematol. 2000;34:27-53.

Huber, et al. In vivo antitumor activity of 5-fluorocytosine on human colorectal carcinoma cells genetically modified to express cytosine deaminase. Cancer Res. Oct. 1, 1993;53(19):4619-26.

Huber, et al. Metabolism of 5-fluorocytosine to 5-fluorouracil in human colorectal tumor cells transduced with the cytosine deaminase gene: significant antitumor effects when only a small percentage of tumor cells express cytosine deaminase. Proc Natl Acad Sci U S A. Aug. 16, 1994;91(17):8302-6.

Hurford, et al. Gene therapy of metastatic cancer by in vivo retroviral gene targeting. Nat Genet. Aug. 1995;10(4):430-5.
Ikuta. Alterations in protein-DNA interactions in the y-globin gene promoter in response to butyrate therapy. Blood. Oct. 15, 1998;92(8);2924-33.
Inati. βThalassemia: the Lebanese experience. Clin Lab Haematol. 2006;(28)217-27.
International search report dated Jan. 2, 1995 for PCT Application No. US94/11565.
International search report dated Oct. 12, 2000 for PCT Application No. US1999/03014.
International search report dated Mar. 2, 2010 for PCT Application No. US2009/069035.
International search report dated Sep. 30, 2006 for PCT Application No. US1996/02907.
Jaffe, et al. Classification of cytotoxic T-Cell and natural killer cell lymphomas. Semin Hematol. 2003;40:175-184.
Jiang. cMYB is involved in the regulation of fetal hemoglobin production in adults. Blood. Aug. 1, 2006;108(3):1077-83.
Jiwa, et al. Epstein-Barr virus DNA in Reed-Sternberg cells of Hodgkin's disease is frequently associated with CR2 (EBV receptor) expression. Histopathology. 1992;21:51-57.
Johansson, et al. Epstein-Barr Virus (EBV)-associated antibody pattern in malignant lymphoma and leukemia. 1. Hodgkin's disease. Int J Cancer. 1970;5:450-462.
Johnson. L-carnitine for treatment of distal ulcerative colitis. Gastroenterology. Nov. 1992;103(5):1709-10.
Jones, et al. T-cell lymphomas containing Epstein-Barr virus DNA in patients with chronic Epstein-Barr virus infections. N Engl J Med. 1988;318(12):733-741.
Kanavaros, et al. Nasal T-cell lymphoma: a clinicopathologic entity associated with peculiar phenotype and with Epstein-Barr virus. Blood. 1983;81(10):2688-2695.
Kato. Deconstructing sickle cell disease: reappraisal of the role of hemolysis in the development of clinical subphenotypes. Blood Rev. Jan. 2007;21(1):37-47.
Kattamis. Treatment of thalassemia with hydroxyurea: an indispensable alternative therapy. J Pediatr Hematol Oncol. Nov. 2007;29(11):729-730.
Kawa. Epstein-Barr virus-associated disease in humans. Int J Hematol. 2000;71:108-117.
Kirk, et al. Arginine stimulates wound healing and immune function in elderly human beings. Surgery. Aug. 1993;114(2):155-9; discussion 160.
Kleer, et al. Detection of Epstein-Barr virus in rapidly growing fibroadenomas of the breast in immunosuppressed hosts. Modern Pathol. 2002;15(7):759-764.
Konstan, et al. Effect of high-dose ibuprofen in patients with cystic fibrosis. New England Journal of Medicine. 1995;332(13):848-854.
Korbjuhn, et al. Frequent latent Epstein-Barr virus infection of neoplastic T cells and bystander B cells in human immunodeficiency virus-negative European peripheral pleomorphic T-cell lymphomas. Blood. 1993;82(1):217-223.
Koren. Response to hydroxyurea therapy in β-thalassemia. Am J Hematol. 2008;83(5):366-70.
Kwong, et al. Natural killer cell lymphoma/leukemia: pathology and treatment. Hematol Oncol. 1997;15:71-79.
Lea, et al. Butyramide and monobutyrin: growth inhibitory and differentiating agents. Anticancer Research. 1993;13:145-149.
Lee, et al. The association of Epstein-Barr virus with smooth-muscle tumors occurring after organ transplantation. N Engl J Med. 1995;332:19-25.
Leoncini, et al. Epstein-Barr virus and gastric cancer: data and unanswered questions. Int J Cancer. 1993;53:898-901.
Liakopoulou, et al. Induction of fetal hemoglobin by propionic and butyric acid derivatives: correlations between chemical structure and potency of HbF induction Blood Cells Mol Dis. 2002;29:48-56.
Liakopoulou, et al. Stimulation of fetal hemoglobin production by short chain fatty acids. Blood. 1995;86(8):3227-3235.
Lilbert, et al. Common vascular changes in the jugular vein of saline controls in continuous infusion studies in the beagle dog. Toxicol. Pathol. 2004;32:694-700.
Little. Metabolic persistence of fetal hemoglobin. Blood. Apr. 1, 1995;85(7):1712-18.
Lokeshwar, et al. Enhancement of radiation response of prostatic carcinoma by taxol: therapeutic potential for late-stage malignancy. Anticancer Res. Jan.-Feb. 1995;15(1):93-8.
Magrath, et al. Breast cancer: a new Epstein-Barr virus-associated disease? J Nat Cancer Inst. 1999;91:1349-1350.
Maia, et al. Chronic, active Epstein-Barr virus infection. Curr Opin Hematol. 2000;7:59-63.
Mankidy, et al. Short-chain fatty acids induce g-globin gene expression by displacement of a HDAC3-NCoR repressor complex. Blood. 2006;108(9):3179-3186.
Mares, et al. Evaluation of gas chromatograph packings for the separation of butyric acid from serum-catalyzed hydrolysis of ethyl butyrate. Anal Biochem. Oct. 15, 1978;90(2):824-8.
Mathias, et al. Ineffective erythropoiesis in β-thalassemia major is due to apoptosis at the polychromatophilic normoblast stage. Exp Hematol. 2000;28:1343-1353.
McClain, et al. Association of Epstein-Barr virus with leiomyosarcomas in young people with AIDS. N Engl J Med. 1995;332:12-18.
Medeiros, et al. Localization of Epstein-Barr viral genomes in angiocentric immunoproliferative lesions. Am J Surg Pathol. 1992;16:439-447.
Meijer, et al. Epstein-Barr virus and human T-cell lymphomas. Seminars in Cancer Biology. Aug. 1996;7(4):191-196.
Miller, et al. Antibodies to butyrate-inducible antigens of Kaposi's Sarcoma-associated herpesvirus to patient with HIV-1 infection. The New England J. of Med. 1996;334(20):1292-1297.
Modell, et al. Epidemiology of haemoglobin disorders in Europe: an overview. Scand J Clin Lab. 2007;67:39-70.
Mueller, et al. Hodgkin's disease and Epstein-Barr virus. Altered antibody pattern before diagnosis. N Engl J Med. 1989;320:689-695.
Nagel, et al. F reticulocyte response in sickle cell anemia treated with recombinant human erythropoietin: a double-blind study. Blood. 1993;1:9-14.
Nagel, et al. Structural bases of the inhibitory effects of hemoglobin F and hemoglobin A2 on the polymerization of hemoglobin S. Biochemistry. 1979;76(2):670-72.
Niedobitek, et al. Epstein-Barr virus gene expression in Hodgkin's disease. Blood. 1991;78:1628-1630.
Niedobitek. The role of Epstein-Barr virus in the pathogenesis of Hodgkin's disease. Ann Oncol. 1996;7:S11-S17.
Nisli, et al. Recombinant Human erythropoietin trial in thalassemia intermedia. J Trop Pediatr. 1996;42:330-34.
Noguchi, et al Inhibition of sickle hemoglobin gelation by amino acids and related compounds. Biochemistry. 1978;17(25):5455-5459.
Noguchi, et al. Levels of fetal hemoglobin necessary for treatment of sickle cell disease. N Engl J Med. Jan. 14, 1988;318(2):96-99.
Nudelman, et al. Novel anticancer prodrugs of butyric acid. 2. J Med Chem. Feb. 21, 1992;35(4):687-94.
Oldfield, et al. Gene therapy for the treatment of brain tumors using intra-tumoral transduction with the thymidine kinase gene and intravenous ganciclovir. Hum Gene Ther. Feb. 1993;4(1):39-69.
O'Malley, et al. Adenovirus-mediated gene therapy for human head and neck squamous cell cancer in a nude mouse model. Cancer Res. Mar. 1, 1995;55(5):1080-5.
Wu, et al. Detection of EBV gene expression in Reed-Sternberg cells of Hodgkin's disease. Int J Cancer. 1990;46:801-804.
Yeivin, et al. Sodium butyrate selectively induces transcription of promoters adjacent to the MoMSV viral enhancer. Gene. Jul. 15, 1992;116(2):159-64.
Zeitlin, et al. Evidence of CFTR function in cystic fibrosis after systemic administration of 4-phenylbutyrate. Mol Ther. Jul. 2002;6(1):119-26.
Zhang, et al. Effect of (E)-5-(2-bromovinyl)-2'-deoxyuridine on several parameters of Epstein-Barr virus infection. J Gen Virol. Jan. 1984;65 ( Pt 1):37-46.
zur Hausen, et al. EBV DNA in biopsies of Burkitt tumours and anaplastic carcinomas of the nasopharynx. Nature. 1970;228(5276):1056-1058.
Volkov, I. I. et al., 1967, CA:66:91411m, abstract.

Wittstruck, et al., 1967, CA:67:59315, abstract.
Canceill et al., 1970, CA:73:65917, abstract.
Faucitano et al., 1967, CA:68:110268, abstract.
Archin, et al. Antiretroviral intensification and valproic acid lack sustained effect on residual HIV-1 viremia or resting CD4+ cell infection. PLoS One. Feb. 23, 2010;5(2):e9390 (p. 1-4).
Archin, et al. Expression of latent HIV induced by the potent HDAC inhibitor suberoylanilide hydroxamic acid. AIDS Res Hum Retroviruses. Feb. 2009;25(2):207-12.
Archin, et al. Expression of latent human immunodeficiency type 1 is induced by novel and selective histone deacetylase inhibitors. AIDS. Sep. 10, 2009;23(14):1799-806.
Archin, et al. Valproic acid without intensified antiviral therapy has limited impact on persistent HIV infection of resting CD4+ T cells. AIDS. Jun. 19, 2008;22(10):1131-5.
El-Beshlawy, et al. Fetal globin induction in beta-thalassemia. Hemoglobin. 2009;33 Suppl 1:S197-203.
Keedy, et al. A limited group of class I histone deacetylases acts to repress human immunodeficiency virus type 1 expression. J Virol. May 2009;83(10):4749-56.
Matalon, et al. The histone deacetylase inhibitor ITF2357 decreases surface CXCR4 and CCR5 expression on CD4(+) T-cells and monocytes and is superior to valproic acid for latent HIV-1 expression in vitro. J Acquir Immune Defic Syndr. May 1, 2010;54(1):1-9.
Perez, et al. Bryostatin-1 Synergizes with Histone Deacetylase Inhibitors to Reactivate HIV-1 from Latency. Curr HIV Res. Sep. 1, 2010;8(6):418-29.
Rubenstein et al., "A pilot clinical trial of oral sodium 4-phenylbutyrate (Buphenyl) in DELTAF508-homozygous cystic fibrosis patients: Partial restoration of nasal epithelial CFTR function." American Journal of Respiratory and Critical Care Medicine 157(2):484-490, 1998.
Walsh et al., "Combination of Drug and Gene Delivery by Gelatin Nanospheres for the Treatment of Cystic Fibrosis." Proceedings of the International Symposium on Controlled Release of Bioactive Materials, U.S., Deerfield, IL, Controlled Release Soc. SYMP, 24:75-76, 1997.
Rubinstein et al., "In vitro pharmacologic restoration of CFTR-mediated chloride transport with sodium 4-phenylbutyrate in cystic fibrosis epithelial cells containing DELTAF508-CFTR." Journal of Clinical Investigation, 10(100):2457-2465, 1997.
Konstan, M et al., "Effect of High-Dose Ibuprofen in Patients with Cystic Fibrosis." New England Journal of Medicine 332(13):848-854, 1995.
Cheng, SH et al., Functional activation of the cystic fibrosis trafficking mutant DELTAF508-CCFTR by expression, Am. J. Physiol. 268:L615-624, 1995.
Egorin, et al. Phase 1 clinical and pharmacokinetic study of hexamethylene bisacetamide (NSC 95580) administered as a five-day continuous infusion. Cancer. Res. 1987;47:617-623.
Ellis, et al. Synthetic human β-globin 5'HS2 constructs function as locus control regions only in multicopy transgene concatamers. EMBO Journal. 1993;12:127-134.
Endo, et al. Differential induction of adult and fetal globin gene expression in the human CML cell subline KU-812F/33. J. Biochem. 1994;115:540-544.
Fathallah, et al. Induction of fetal hemoglobin in the treatment of sickle cell disease. American Society of Hematology. 2006:55-62.
Fibach, et al. Enhance fetal hemoglobin production by Phenylacetate and 4-Phenylbutyrate in erythroid precursors derived from normal donors and patients with sickle cell anemia and b-Thalassemia. Blood. 1993;82(7):2203-2209.
Flyer, et al. Retrovirus-induced changes in major histocompatibility complex antigen expression influence susceptibility to lysis by cytotoxic T lymphocytes. The Journal of Immunology. Oct. 1985;135(4):2287-92.
Forrester, et al. Molecular analysis of the humanβ-globin locus activation region. Proc. Natl. Acad. Sci. USA. 1989;86:5439-5443.
Foss, et al. Biomodulatory effects of butyric acid derivatives on leukemia and lymphoma cells. Blood. 1993; 82/10 Suppl. 1:564A. (1993) The American Society of Hematology, 35th Annual Meeting, Dec. 3-7, Abstract only.
Fraser, et al. Each hypersensitive site of the human β-globin locus control region confers a different developmental pattern of expression on the globin genes. Genes Dev. 1993;7:106-13.
Fritsch, et al. Characterisation of deletions which affect the expression of fetal globin genes in man. Nature. 1979;279:598-603.
Gabbianelli, et al. Granulocyte-macrophage colony-stimulating factor reactivates fetal hemoglobin synthesis in erythroblast clones from normal adults. Blood. Dec. 1989;74(8):2657-67.
Garre, et al. Regulation of acetylcholinesterase expression in the K-562 cell line. Cancer Research. Sep. 1984;44:3749-3751.
Garsetti, et al. Butyric acid-induced differentiation of HL-60 cells increases the expression of a single lysophospholipase. Biochem. J. 1992;288:831-837.
Gaudet, et al. Differential regulation of arylamine and arylalkylamine N-acetyltransferases in human retinoblastoma (Y-79) cells. Neurochem Int. 1993;22(3):271-275.
Gerharz, et al. Modulation of invasive potential in different clonal subpopulations of a rat rhabdomyosarcoma cell line (BA-HAN-1) by differentiation induction. Clin. Exp. Metastasis. 1993;11(1):55-67.
Ghanayem, et al. Structure-activity relationships for the in vitro hematotoxicity of N-alkoxyacetic acids, the toxic metabolites of glycol ethers. Chem.-Biol. Interactions. 1989;70:339-352.
Ginder, et al. Activiation of a chicken embryonic globin gene in adult erythroid cells by 5-Azacytidine and sodium butyrate. Proc. Natl. Acad. Science, USA. Jul. 1984;81:3954-3958.
Grossi, et al., Effects of monosaccharide esters of butyric acid on the synthesis of hemoglobin T chain and erythroleukemis cell line, Abstract of ASH Annual Meeting, Seattle, WA, Dec. 1-5, 1995.
Guilbaud, et al. Effects of differentiation-inducing agents on maturation of human MCF-7 breast cancer cells. Journal of Cellular Physiology. 1990;145:162-172.
Harig, et al. Treatment of diversion colitis with short-chain-fatty acid irrigation. N. Engl. J. Med. 1989;320(1):23-28.
Henle, et al. Relation of Burkitt's tumor-associated herpes-type virus to infectious mononucleosis. Proc Natl Acad Sci USA. 1968;58:94-101.
Hock, et al., Retrovirus-mediated transfer and express of drug resistance genes in human hematopoietic progenitor cells. Nature. Mar. 20, 1986;320:275-277.
Hoessly, et al. Factors responsible for variable reported lineages of HL-60 cells induced to mature with butyric acid. Cancer Research. Jul. 1, 1989;49:3594-97.
Hoey, et al. Molecular cloning and functional analysis of drosophila TAF110 reveal properties expected of coactivators. Cell. 1993;72:247-60.
Huang, et al. The hematopoietic growth factor KL is encoded by the SI locus and is the ligand of the o-kit receptor, the gene product of the W locus. Cell. Oct. 5, 1990;63:225-233.
Jane, et al. Hemoglobin switching in man and chicken is mediated by a heteromeric complex between the ubiquitous transcription factor CP2 and a developmentally specific protein. The EMBO Journal. 1995;14(1): 97-105.
Karlsson, et al. Developmental regulation of human globin genes. Ann. Rev. Biochem. 1985;54:1071-1108.
Kim, et al. Modification of thermosensitivity of HeLa cells by sodium butyrate, dibutyrl cyclic adenosine 3':5'-monophosphate, and retinoic acid. Cancer Research. Feb. 1984;44:697-702.
Koeffler. Induction of differentiation of human acute myelogenous leukemia cells: therapeutic implications. Blood. 1983;62:709-721.
Krantis, et al. Augmentation of cysteamine-induced ulceration of rat duodenum by systemically administered g-Aminobutyric Acid (GABA). Digestive Diseases and Sciences. Aug. 1989;34(8m):1211-1216.
Labie, et al. Common haplotype dependency of high Gg-globin gene expression and high Hb F levels in b-thalassemia and sickle cell anemia patients. Proc. Natl. Acad. Sci. USA. Apr. 1985;82:2111-2114.
Langdon, et al. Effect of sodium butyrate and other differentiation inducers of poorly differentiated human ovarian adenocarcinoma cell lines. Cancer Research Nov. 1, 1988;48:6161-6165.
Leavitt, et al. Butyric acid suppression of the in vitro neoplastic state of Syrian hamster cells. Nature. Jan. 1978;271(19):262-65.

Leder, et al. Differential of erythroleukemic cells in the presence of inhibitors of DNA synthesis. Science. Jul. 14, 1975;190:893-894.

Letvin, et al. Augmentation of fetal-hemoglobin production in anemic monkeys by hydroxyurea. The New England Journal of Medicine. 1984;310(14):869-873.

Ley, et al. 5-Azacytidine increases γ-globin synthesis and reduces the proportion of dense cells in patients with sickle cell anemia. Blood. 1983; 62(2):370-380.

Ley, et al. 5-Azacytidine selectively increases γ-globin synthesis in a patient with β+thalassemia. The New England Journal of Medicine. 1982;307(24):1469-1475.

Liakopoulou, et al. Structural features of short chain fatty acid-derived inducers of fetal hemoglobin. Abstract of ASH Annual Meeting, Seattle, WA, Dec. 1-5, 1995.

Maziarz, et al. Distinct effects of interferon-g and MHC class 1 surface antigen levels on resistance of the K562 tumor cell line. Cellular Immunology. 1990;130:329-38.

Maziarz, et al. The regulation of exogenous and endogenous class I MHC genes in a human tumor cell line, K562. Molecular Immunology. 1990;27:135-142.

McCafferty et al. Inhibition of butyric acid-induced colitis in mice by 16, 16-dimethyl prostaglandin E2. Inflammation Research. Mar. 1992;36 Suppl 1:C79-81.

McCafferty, et al. Short chain fatty acid-induced colitis in mice. Int. J. Tissue React. 1989;11(4):165-168.

McDonagh, et al. The Upstream Region of the Human γ-globin Gene Promoter. J. Biol. Chem. 1991;266:11965-74.

Migliaccio, et al. Influence of recombinant hematopoietins and of fetal bovine serum on the globin synthetic pattern of human BFUe. Blood. 1990;76:1150-1157.

Takahashi, et al. Differentiation of cultured friend leukemia cells induced by short-chain fatty acids. Gann. Oct. 1975;66:577-580.

Torrealba-De Ron, et al. Perturbations in the erythroid marrow progenitor cell pools may play a role in the augmentation of HbF by 5-azacytidine. Blood. 1984;63(1):201-210.

Tsao, et al. Differential effects of sodium butyrate, dimethyl sulfoxide, and retinoic acid on membrane-associated antigen, enzymes, and glycoproteins of human rectal adenocarcinoma cells. Cancer Research. Mar. 1982;42:1052-1058.

Tuan, et al. Different 3' end points of deletions causing δβ-thalassemia and hereditary persistence of fetal hemoglobin: Implications for the control of γ-globin gene expression in man. Proc. Natl. Acad. Sci. USA. 1983;80:6937-6941.

Ulrich. Function of normal and mutated gamma-globin gene promoters in electroporated K562 erythroleukemia cells. Blood. 1990;75:990-99.

Wasseman, et al. Different effects of sodium butyrate and dimethylsulfoxide on gamma-glutamyl transpeptidase and allcaline phosphatase activities in MCF-7 breast cancer cells. Expl. Cell Biol. 1987;55:189-193.

Watson, et al. Butyrate acid in the treatment of cancer. The Lancet. 1933:746-748.

Williams, et al. Identification of a Ligand for the o-kit Proto-Oncogene. Cell. Oct. 5, 1990;63:167-174.

Wood, et al. Hb F Synthesis in Sickle Cell Anaemia: a Comparison of Saudi Arab Cases with those of African Origin. British Journal of Haematology. 1980;45:431-445.

Young, et al. Phase I trial and clinical pharmacological evaluation of hexamethylene bisacetamide administration by ten-day continuous intravenous infusion at twenty-eight-day intervals. Cancer Res. 1988;48:7304-7309.

Zituik, et al. The Silencing of .gamma.-Globin Gene Exin a .beta.-Globin Locus Yac can be Arrested by a .alpha.-Aminobutyric Acid. Abstract of ASH Annual Meeting, Seattle, Washington, Dec. 1-5, 1995.

Zsebo, et al. Identification, purification and biological characterization of hematopoietic stem cell factor from buffalo rat liver-conditioned medium. Cell. Oct. 5, 1990;63:195-201.

Zsebo, et al. Stem cell factor is encoded at the si locus of the mouse and is the ligand for the o-kit tyrosine kinase receptor. Cell. Oct. 5, 1990;63:213-224.

Miller, et al. Clinical pharmacology of sodium butyrate in patients with acute leukemia. Eur J Cancer Clin Oncol. 1987;23(9):1283-1287.

Miller, et al. Influence of steel factor on hemoglobin synthesis in sickle cell disease. Blood. 1992;79:1861-1868.

Miller, et al. Toxicity of methoxyacetic acid in rats. Fundamental and Applied Toxicology. 1982; 2:158-160.

Moi, et al. Synergistic enhancement of globin gene expression by activator protein-1-like proteins. Proc. Natl. Acad. Sci. USA. 1990;87:9000-9004.

Morita, et al. Effect of sodium butyrate on alkaline phosphatase in HRT-18, a human rectal cancer cell line. Cancer Research. Nov. 1982;42:4540-4545.

Mueller, et al. In vivo footprinting of a muscle specific enhancer by ligation mediated PCR. Science. 1989;246:780-786.

Nagai, et al. Studies on the synogistic action and anti-ulcerous activity of cortisone-GABOB. Arzneim-Forsch. 1971;21(1):96-97.

Naguib, et al. Effects of N,N-dimethylformanide and sodium butyrate on enzymes of pyrimidine metabolism in cultured human tumor cells. Leukemia Research. 1987;11(10):855-861.

Nathan. Regulation of fetal hemoglobin synthesis ini the hemoglobinopathics. Annals New York Academy of Sciences, Fifth Cooley's Symposium. 1985;445:177-187.

Newman, et al. Sodium n-butyrate enhancement of prostaglandin D2 antitumor efficacy. Biochemical Pharmacology. 1985;34(20):3771-3774.

Newman, et al., Induction of the insulin receptor and other differentiation markers by sodium butyrate in the Burkitt lymphoma cell, Raji. Biochemical and Biophysical Research Communications. May 30, 1989;161(1):101-106.

Ney, et al. Tandem AP-1-binding sites within the human β-globin dominant control region function as an inducible enhancer in erythroid cells. Genes Dev. 1990;4:993-1006.

Nienhuis, et al. Pharmacological manipulation of fetal hemoglobin synthesis in patients with severe β-Thalassemia. Ann N Y Acad Sci. vol. 445, Fifth Cooley's Anemia Symposium, Jun. 21, 1985:198-211.

Novogrodsky, et al. Effect of polar organic componds on leukemic cells. Cancer. Jan. 1, 1983;51:9-14.

Nudel, et al. Different effects of chemical inducers on expression of β globin genes in murine erythroleukemia cells. Proc. Natl. Acad. Sci. USA. Mar. 1977;74(3):1100-1104.

Oliva, et al. Histone hyperacetylation can induce unfolding of the nucleosome core particle. Nuc. Acids Res. 1990;18:2739-2747.

Ormandy, et al. Coordinate regulation of oestrogen and prolactin receptor expression by sodium butyrate in human breast cancer cells. Biochemical and Biophysical Research Communications. Jan. 31, 1992;182(2):740-745.

Partington, et al. Human globin gene transcription in injected xenopus cocytes: enhancement by enhancement by sodium butyrate. EMBO J. Dec. 1, 1984;3(12):2787-92.

Patel, et al. Transcriptional activation potential of normal and tumor-associated myb isoforms does not correlate with their ability to block GCSE- induced terminal differentiation of murine myeloid precursor cells. Oncogene. 1996;13:1197-1208.

Perrine, et al. A short-term trial of butyrate to stimulate fetal-globin-gene expression in the β-globin disorders. N. Engl. J. Med. 1993;328:81-86.

Perrine, et al. An Interleukin 2/Sodium Butyrate combination as immunotherapy for rat colon cancer peritoneal carcinomatosis. Gasteroenterology. 1994;107:1697-1708.

Perrine, et al. Butryic acid analogues augment γ globin gene expression in neonatal erthroid progenitors. Biochemical and Biophysical Research Communication. 1987;148:694-700.

Perrine, et al. Butyrate derivatives, new agents for stimulating fetal globin production in the β-globin disorders. The American Journal of Pediatric Hematology/Oncology. 1994;16(1):67-71.

Perrine, et al. Isobutyramide, an orally bioavailable butyrate analogue, stimulates fetal globin gene expression in vitro and in vivo. British Journal of Hematology. 1994:555-561.

Perrine, et al. Sodium butyrate enhances fetal globin gene expression in erythroid progenitors of patients with Hb SS and beta thalassaemia. Blood. 1989;74:454-459.

Planchon, et al. Differential effects of butyrate derivatives on human breast cancer cells grown as organotypic nodules in vitro and as xenografts in vivo. In Vivo. Nov.-Dec. 1992;6(6):605-10.

Planchon, et al. Morphology and intermediate filament composition of human mammary epithelial cells treated with stable butyrate derivative. Anticancer Res. Nov.-Dec. 1992;12(6B):2315-20.

Platt, et al. Mortality in sickle cell disease—life expectancy and risk factors for early death. N. Engl. J. Med. 1994;330:1639-1644.

Pouillart, et al. Enhancement by stable butyrate derivatives of antitumor and antiviral actions of interferon. Int. J. Cancer. 1992;51:596-601.

Prasad. Butyric acid a small fatty acid with diverse biological functions. Life Sciences. 1980;27:1351-1358.

Prochownik, et al. Deregulated expression of o-myc by murine erythroleukemia cells prevents differentiation. Nature. Aug. 28, 1986;322:848-50.

Reiss, et al. Induction of tumor cell differentiation as a therapeutic approach: preclinical models for hematopoietic and solid neoplasms. Cancer Treatment Reports. Jan. 1986;70(1):201-218.

Rephaeli, et al. Anti-lekemic effect of butyrate in-vitro and in-vivo and the development of a potent butyrate prodrug. Blood. 1990;76:115a.

Rius, et al. The induction of vimentin gene expression by sodium butyrate in human promonocytic leukemia U937 cells. Experimental Cell Research. 1990;188:129-134.

Rodgers, et al. Augmentation by erythropoietin of the fetal-hemoglobin response to hydroxyurea in sickle cell disease. The New England Journal of Medicine. 1993;328(2):73-80.

Roediger, et al. Selective reduction of fatty acid oxidation in colonocytes: correlation with ulcerative colitis. Lipids. 1990;25(10):646-652.

Rowinsky, et al. Prolonged infusion of hexamethylene bisacetamide: a phase I and pharmacological study. Cancer Res. 1987;47:5788-5795.

Sachs. Cell differentiation and bypassing of genetic defects in the suppression of malignancy. Cancer Research. 1987;47:1981-1986.

Safaya, et al. Augmentation of g-globin gene promoter activity by carboxylic acids and components of the human β-glovin locus control region. Blood. Dec. 1, 1994;84(II):3929-3925.

Scheppach, et al. Effect of butyrate enemas on the colonic mucosa in distal ulcerative colitis. Gastroenterology. Jul. 1992;103(1):51-6.

Seifter, et al. An outlier theory of cancer curability—tumor cell differentiation as a therapeutic goal. The American Journal of Medicine. Oct. 1987;83:757-60.

Slamon, et al. Expression of cellular oncogenes in human malignancies. Science. 1984;224:256-262.

Stamatoyannopolous, et al. Fetal hemoglobin induction by acetate, a product of butyrate catabolism. Blood. Nov. 1, 1994;84(9):3198-204.

Stamatoyannopolous, et al. The regulation of hemoglobin switching. The Johns Hopkins University Press. 1990:425-426.

Sutherland, et al. Induction of the expression of HLA class I antigens on K562 by interferons and sodium butyrate. Human Immunology. 1985;12:65-73.

Abbott, et al. Quantitative structure-anticonvulsant activity relationships of valproic acid, related carboxylic acids and tetrazoles. Neuropharmacology. Mar. 1988;27(3):287-94.

Abe, et al. Sodium butyrate induction of milk-related antigens in human MCF-7 breast carcinoma cells. Cancer Research. Oct. 1984;44:4574-4577.

Abraham, et al. Design, synthesis, and testing of potenital antisickling agents. 1. Halogenated Benzyloxy and Phenoxy Acids. J. Med. Chem. 1982;25:1015-17.

Abraham, et al. Synthesis of the minor fetal hemoglobin Fic in colonies of erythropoietic precursors isolated from human umbilical cord blood. American Journal of Hematology. 1982;12:207-213.

Al-Khatti, et al. Erythropoietin stimulates F-reticulocyte formation in sickle cell anemia. Trans. Assoc. Am. Physicians. 1988;101:54-61.

Anderson, et al. Molecular cloning of mast cell growth factor, a hematopoietin that is active in both membrane bound and soluble forms. Cell. Oct. 5, 1990;63:235-243.

Andrews, et al. A rapid micropreparation technique for extraction of DNA-binding proteins from limiting numbers of mammalian cells. Nucl. Acids Res. 1991;19:2499-2500.

Andrews, et al. Erythroid transcription factor NF-E2 is a haematopoietic-specific basic-leucine zipper protein. Nature. 1993;362:722-728.

Augeron, et al. Emergence of permanently differentiated cell clones in a human colonic cancer cell line in culture after treatment with sodium butyrate. Cancer Research. Sep. 1984;44:3961-3969.

Barker, et al. The actions of cyclic AMP, its butyryl derivatives and Na butyrate on the proliferation of malignant trophoblast cells in vitro, Br. J. Cancer. 1977;35:314-321.

Barton, et al. The erythroid protein cGATA-1 Functions with a stage-specific factor to activate transcription of chromatin-assembled b-globin genes. Genes & Development. 1993;7:1796-809.

Bartram, et al. Proliferation of human colonic mucosa as an intermediate biomarker of carcinogenesis: effects of butyrate, deoxycholate, calcium, ammonia, and pH. Cancer Research. Jul. 15, 1993;53:3283-3288.

Belcheva, et al. Up-regulation of delta opioid receptors in neuroblastoma hybrid cells: evidence for differences in the mechanisms of action of sodium butyrate and naltrexone. J Pharmacol Exp Ther. Oct. 1991;259(1):302-9.

Bernards, et al. Physical mapping of the globin gene deletion in hereditary persistence of foetal haemoglobin (HPFH). Nucleic Acids Research. 1980;8(7):1521-1534.

Bloch. Induced cell differentiation in cancer therapy. Cancer Treatment Reports. 1984;68:199-205.

Boulikas. Poly (ADP-ribose) synthesis in blocked and damaged cells and its relation to carcinogenesis. Anticancer Res. 1992;12(3):885-898.

Bourgeade, et al. Enhancement of interferon anti-tumor action by sodium butyrate. Cancer Res. 1979;39:4720-4723.

Breitman, et al. Combinations of retinoic acid with either sodium butyrate, dimethyl, sulfoxide, or hexamethylene bisacetamide synergistically induce differentiation of the human myeoid leukemia cell line HL60. Cancer Research. 1990;50:6268-6273.

Breuer, et al. Rectal irrigation with short-chain fatty acids for distal ulcerative colitis. Dig. Dis. Sci.1991;36(2):185-187.

Bugaut, et al. Biological effects of short-chain fatty acids in nonruminant mammals. Amex. Rev. Nutr.1993;13:217-241.

Burns, et al. Butyrate induces selective transcriptional activation of a hypomethylated embryonic globin gene in adult erythroid cells. Blood. 1988;72(5):1536-1542.

Byrd, et al. Two types of transglutaminase in the PC12 pheochromocytoma cell line. The Journal of Biological Chemistry. Aug. 25, 1987;262(24):11699-11705.

Callery, et al. Identification of metabolites of the cell-differentiating agent hexamethylene bisacetamide in humans. Cancer Res. 1986;46:4900-4903.

Chany, et al. Antitumor effect of arginine butyrate in conjunction with corynebacterium and interferon. Int. J. Cancer. 1982;30:489-93.

Chany, et al. Effect of coordinated therapeutic assays using C. Parvum, Interferon and Arginine Butyrate on spontaneous disease and survival of AKR mice. Int. J. Cancer. 1993;32:379-383.

Charache, et al. Treatment of sickle cell anemia with 5-azacytidine results in increased fetal hemoglobin production and is associated with nonrandom hypomethylation of DNA around the gamma-delta-beta-globin gene complex. Proc. Natl. Acad. Sci. USA. 1983;80:4842-4846.

Charache, et al., Hydroxyurea-induced augmentation of fetal hemoglobin production in patients with sickle cell anemia. Blood. 1987;69(1):109-116.

Chen, et al. Tributyrin: a prodrug of butyric acid for potential clinical application in differentiation therapy. Cancer Research. Jul. 1, 1994;54:3494-3499.

Clegg, et al. Abnormal human haemoglobins. Separation and characterization of the alpha and beta chains by chromatography, and the determination of two new variants, hb Chesapeak and hb J (Bangkok). J Mol Biol. Aug. 1966;19(1):91-108.

Collins, et al. Oral sodium phenylbutyrate therapy in homozygous $ thalassemia: a clinical trial. Blood. Jan. 1, 1995;85(1):43-49.

Constantaoulakis, et al. On the induction of fetal hemogloving by butyrates: in vivo and in vitro studies with sodium butyrate and comparison of combination treatments with 5-AzaC. Blood. Nov. 1, 1989;74(6):1963-1971.

Cook, et al. Effect of sodium butyrate on α-Fetoprotein gene expression in rat hepatoma cells in vitro. Cancer Research. Jul. 1985;45:3215-3219.

Copeland, et al. Mast cell growth factor maps near the steel locus on mouse chromosome 10 and is deleted in a number of steel alleles. Cell. Oct. 5, 1990;63:175-183.

Cossman, et al. Induction of differentiation in a case of common acute lymphoblastic leukemia. The New England Journal of Medicine. Nov. 11, 1982;307(20):1251-54.

Daniel. Pharmacokinetic study of butyric acid administered in vivo as sodium and arginine butyrate salts. Clinica Chimica Acta. 1989;181:255-264.

De Vente, et al. Effects of adenosine and adenosine-analogs on adenylate cyclase activity in the rat adipocyte plasma membrane: comparison of the properties of the enzyme with $Mn^{2*}$ and $Mg^{2+}$ as divalent cations. Molecular and Cellular Biology. 1981;40:65-73.

Dover, et al. Induction of fetal hemoglobin production in subjects with sickle cell anemia by oral sodium phenylbutyrate. Blood. 1994;84:339-343.

Dover, et al. Ilydroxyurea induction of hemoglobin F production in sickle cell disease: relationship between cytotoxicity and F cell production. Blood. 1986;67:735-38.

2,2-DIMETHYLBUTYRIC ACID ORAL PHARMACEUTICAL COMPOSITIONS

CROSS-REFERENCE TO RELATED APPLICATIONS

This Application is a Continuation Application of U.S. Ser. No. 11/827,362, filed Jul. 11, 2007 now abandoned, which is a Divisional Application and claims the benefit under 35 U.S.C. §120 of U.S. Ser. No. 10/185,745, filed Jul. 1, 2002, now U.S. Pat. No. 7,265,153, which is a Divisional Application and claims the benefit under 35 U.S.C. §120 of Ser. No. 09/248,260, filed Feb. 11, 1999, now abandoned, which claims the benefit under 35 U.S.C. §119(e) of U.S. Provisional Application 60/074,304, filed Feb. 11, 1998.

FIELD OF THE INVENTION

The invention relates to pharmaceutically acceptable compositions for administration to humans to treat cystic fibrosis and also to methods for effectively utilizing these compositions.

BACKGROUND OF THE INVENTION

Cystic fibrosis (CF) is a systemic disorder that results when mutations in the cystic fibrosis transmembrane conductance regulator (CFTR), an apical membrane glycoprotein, lead to a reduction in apical membrane chloride transport. CFTR is a cAMP-dependent chloride channel that regulates fluid composition in the respiratory and gastrointestinal tracts. CF is a heritable disease that follows an autosomal recessive pattern of transmission. It is the most common invariably lethal genetic disease in the United States, with frequency among Caucasians being one in two thousand. One in twenty are carriers of the defective gene. CF is characterized by abnormal endocrine and exocrine gland function. In CF, unusually thick mucus leads chronic pulmonary disease and respiratory infections, insufficient pancreatic and digestive function, and abnormally concentrated sweat. Seventy percent of the mutant CFTR alleles in the Caucasian population result from deletion of phenylalanine at position 508 ($\Delta$F508-CFTR), the result of a three base pair deletion in the genetic code. Other mutations have also been described and many may exist. The $\Delta$F508-CFTR mutation results in a CFTR protein capable of conducting chloride, but absent from the plasma membrane because of aberrant intracellular processing. Under usual conditions (37° C.), the $\Delta$F508-CFTR protein is retained in the endoplasmic reticulum (ER), by prolonged association with the ER chaperones, including calnexin and hsp70. The retained CFTR protein is then targeted for degradation by the ubiquitin proteasome pathway. Over expression of $\Delta$F508-CFTR can result in $\Delta$F508-CFTR protein appearing at the cell surface, and this protein is functional once it reaches the cell surface. The $\Delta$F508 "trafficking" block is also reversible by incubation of cultured CF epithelial cells at reduced temperatures (25-27° C.). Lowered temperature results in the appearance of CFTR protein and channel activity at the cell surface, suggesting an intrinsic thermodynamic instability in $\Delta$F508-CFTR at 37° C. that leads to recognition of the mutant protein by the ER quality control mechanism, prevents further trafficking, and results in protein degradation. High concentrations of glycerol (1 M or 10%), a protein stabilizing agent or chemical chaperone, also appears to facilitate movement of $\Delta$F508-CFTR from the ER to the plasma membrane.

Some of the palliative treatments involve the administration of biologically active proteins or chemical compounds to decrease the viscosity of secretions, or to suppress chronic infections of the airways. These treatments have a number of limitations, and do not address the illness directly, but rather attempt to treat the symptoms. Some require continuous use at fairly high doses while others have short effective half-lives. Tolerance to the active ingredient often develops rendering the composition functionally useless. In addition to problems associated with tolerance, the substances themselves or their metabolic by-products or carriers can quickly reach toxic levels in the patient's system which impair kidney or liver function. Further, the chemical compounds themselves can be rapidly destroyed by catabolic enzymes, found in the cells and serum such as aminases, oxidases and hydrolases. Many of these enzymes are also found in hepatic cells, the principal sites for cleansing of the blood. Those able to survive cellular and hepatic catabolic processes are quickly eliminated from the patient's system by the kidneys. Consequently, in vivo retention times for active compounds are extremely short and the ability to achieve any sort of sustained biological effect becomes nearly impossible or, at least, impractical.

Gene therapy for cystic fibrosis has been attempted, but has not been successful to date for a number of reasons, including problems with delivery of the gene to airway cells, insufficient levels of gene expression, inadequate duration of gene expression, and toxicity of the gene therapy preparations.

A recent publication used 4-phenylbutyrate (4PBA) to enable a greater fraction of $\Delta$F508-CFTR to escape degradation and appear at the cell surface (Rubenstein, R. C., Egan, M. E., and Zeitlin, P. L. In vitro pharmacologic restoration of CFTR-mediated chloride transport with sodium 4-phenyl butyrate in cystic fibrosis epithelial cells containing delta-F508-CFTR. J. Clin. Invest. 100:2457-65, 1997). Briefly, primary cultures of nasal polyp epithelia from CF patients ($\Delta$F508 homozygous or heterozygous), or the CF bronchial epithelial cell line IB3-1 ($\Delta$F508/W1282X) were exposed to 4PBA for up to 7 days in culture. 4PBA treatment at concentrations of 0.1 and 2 mM resulted in the restoration of forskolin-activated chloride secretion. Protein kinase A-activated, linear, 10 pS chloride channels appeared at the plasma membrane of IB3-1 cells at the tested concentration of 2.5 mM 4PBA. Treatment of IB3-1 cells with 0.1-1 mM 4PBA and primary nasal epithelia with 5 mM 4PBA also resulted in the appearance of higher molecular mass forms of CFTR, consistent with addition and modification of oligosaccharides in the Golgi apparatus, as detected by immunoblotting of whole cell lysates with anti-CFTR antisera. Immunocytochemistry in CF epithelial cells treated with 4PBA was consistent with increasing amounts of $\Delta$F508-CFTR.

As 4PBA is an analogue of butyrate, a known transcriptional regulator of CFTR expression (Cheng, S. H., Fang, S. L., Zabner, J., Marshall, J., Piraino, S., Schiavi, S. C., Jefferson, D. M., Welsh, M. J., and Smith, A. E. Functional activation of the cystic fibrosis trafficking mutant $\Delta$F508-CFTR by expression. Am. J. Physiol. 268:L615-24, 1995), it was hypothesized that 4PBA might increase transcription of the $\Delta$F508-CFTR allele (Rubenstein et al.). If it were a transcriptional regulator, 4PBA might thereby increase levels of $\Delta$F508-CFTR protein, and by mass action, would force some $\Delta$F508-CFTR to bypass quality control in the ER. Such a mechanism would be consistent with the observations that butyrate itself can induce cAMP-responsive chloride secretion in a $\Delta$F508-homozygous pancreatic acinar cell line (Cheng et al.). The results observed were consistent with 4PBA increasing the amount of $\Delta$F508-CFTR protein produced, but their data demonstrated that this was not due to a transcriptional regulatory effect of 4PBA on the CFTR gene.

In immunoblot experiments, increased CFTR immunoreactivity was observed in the 4PBA-treated samples. Increased CFTR immunoreactivity was also observed by immunocytochemistry after 4PBA treatment, but no changes in CFTF RNA levels were found with 4PBA treatment. The authors further stated that butyrate and 4PBA have effects in 1133-1 cells that are qualitatively different from one another. Respiratory epithelial cells treated with 1-2 mM 4PBA are healthy, grow at a similar rate and with a similar morphology to control cells, and express CFTR channel activity at the plasma membrane. Equimolar concentrations of butyrate caused morphologic changes in IB3-1 cells, with rounding of cells and decreased growth rate.

This seems to indicate that 4PBA and butyrate may have different toxicity profiles and dose-response relationships. In addition, other published observations with butyrate in ΔF508-CFTR transfected C-127 cells found that the ~180-kD mature glycosylated species of CFTR was not observed after 5 mM butyrate treatment for 24 hours, despite a massive increase in ΔF508-CFTR mRNA as demonstrated by Northern analysis (Cheng et al.). This data thus did not demonstrate any effects of butyrate on CFTR protein levels or function, only changes in cellular morphology and cell death (Rubenstein et al.). Rubenstein et al observed no increases in CFTR mRNA in response to 4PBA and indicated that the mechanism of action of 4PBA was not similar to that of butyrate or related to increasing ΔF508-CFTR transcription. In addition, no increases in cAMP-stimulation was observed which would be indicative of chloride ion transport even after treatment with up to 300 mM butyrate (Cheng et al.).

These data argue against any beneficial or therapeutic effect of butyrate on cystic fibrosis. In fact, some authors even stated that butyrate is likely too toxic to use clinically (Rubenstein et al.). Further, the authors made a strong case that 4PBA, which was indicated to be possibly clinically useful, works though a mechanism, which although unknown, is different from butyrate. Taken together, the use of butyrate, and the newer butyrate-derived compounds claimed, as CF therapeutics is contra-indicated according to these reports. Moreover, 4PBA has been used in a few CF patients clinically, but was not well tolerated due to large number of pills required (i.e. very short half-life), and other side effects and, in consideration, that study was terminated.

DESCRIPTION OF THE INVENTION

As embodied and broadly described herein, the present invention is directed to novel chemicals and novel pharmaceutical compositions comprising these and other chemicals that can be used in the treatment and prevention of diseases and disorders associated with cystic fibrosis. The invention is further directed to methods for the administration of these pharmaceutical compositions to patients for the treatment of cystic fibrosis and prevention of its signs and symptoms.

It has been discovered that a group of chemicals and pharmaceutical compositions containing one or more such chemicals are surprisingly successful in the treatment of cystic fibrosis and other disorders including, for example, disorders of blood production. Also surprisingly, it was discovered that many of these compositions are even more effective when administered to a patient in pulses. Pulse therapy is not a form of discontinuous administration of the same amount of a composition over time, but comprises administration of the same dose of the composition at a reduced frequency or administration of reduced doses.

According to these methods, cystic fibrosis and other disorders can be effectively treated and without unnecessary adverse side effects to the patient. Although most compositions are generally safe and non-toxic at therapeutic doses, pulsed administration further reduces risks associated with, for example, toxicity, allergic reactions, the build-up of toxic metabolites and inconveniences associated with conventional treatment. In addition, these chemical compositions, now useful at a substantially reduced dose and frequency, have a significantly reduced risk of complications such as, for example, induced tolerance. These compositions are not inactivated by cellular enzymes or cleared from cells and organs prior to having the desired effect. Further, long-term therapy, typically required for the amelioration of many blood disorders, can be successfully performed. Consequently, doses necessary for maintaining a constant effect for the patient are steady and material costs and inconveniences associated with administration are substantially reduced.

The mechanism of action of many of the chemical compounds or active ingredients of compositions for the treatment of cystic fibrosis involves effecting one or more of the processes of gene transcription, protein translation or processing or transport or stability, cell proliferation, cell recruitment, cell differentiation, or CFTR expression or activity. Gene expression can be increased or decreased by altering chromatin and/or nucleosome structure to render a genetic element more or less susceptible to transcription, by altering DNA structure, for example, by methylation of G residues, by affecting the activity of cell-specific transcription or translation factors such as activators or repressors, or by increasing the rate of transcription or translation. CFTR expression can be increased or decreased by affecting gene expression, peptide expression, CFTR assembly, CFTR glycosylation or transport through the Golgi apparatus or the stability of the CFTR molecule. Cell proliferation may be increased, for example, by stimulating stem cells, pulmonary or pancreatic or other secretory cell growth, or decreased, for example, by effecting a cell's period in or ability to transverse a stage (S, G2, G1, M) of the cell cycle. Cell recruitment may be promoted through the expression of specific cytokines such as cell surface receptors or secreted factors. CFTR function may be increased by promoting chloride transport or other activities of the protein.

Chemical agents that can be administered as pharmaceutical compositions include phenoxyacetic acid, methoxyacetic acid, butyric acid ethyl ester, cinnamic acid, hydrocinnamic acid, alpha-methyl cinnamic acid and alpha-methylhydrocinnamic acid (alpha-MHCA) which stimulate alterations in binding or removal of transcription factors from the proximal promoter region of certain genes or gene clusters and thereby increase suppressed gene expression, or serve a chaperones to facilitate processing, transport and the thermal or physical stability of mutated or normal CFTR proteins.

These compositions preferably increase the expression of CFTR, increase the expression of CFTR genes, increase the number of CFTR-expressing cells or increase the activity of CFTR. Preferably, compositions also increase CFTR expression or function greater than about 30%, more preferably greater than about 100%, and even more preferably greater than about 200%. CFTR intracellular and cell surface expression, gene expression and cell proliferation can be assayed by measuring fold increases in expressed amounts of specific mRNA, protein or numbers of CFTR-expressing cells in treated samples as compared to untreated controls. Utilizing this criteria, compositions preferably increase the amount of CFTR cell surface expression, the amount of CFTR gene expression, the number of CFTR-expressing cells by greater than or equal to about 1½-fold, preferably about two-fold and more preferably about four-fold. CFTR function can be measured by analysis of chloride ion transport/efflux (cAMP-stimulated or otherwise), patch clamping, sweat testing, or improvement in the symptoms of cystic fibrosis.

One embodiment of the invention is directed to pharmaceutical compositions comprising one or more novel chemical agents. Agents include chemicals of the structure $R_1$—$R_2$—$R_3$ or, preferably, $R_1$—C(O)—$R_2$—$R_3$ wherein $R_1$ is $CH_x$, CO, $H_x$, $NH_x$, $OH_x$, $SH_x$, $COH_x$, $CONH_x$, COOH or $COSH_x$; $R_2$ is $CH_x$ or a branched or linear alkyl chain; $R_3$ is $CONH_x$, $COSH_x$, COOH, $COOR_4$, $COR_4$, CO or $OR_4$; $R_4$ is $CH_x$, CO, $H_x$, $NH_x$, $OH_x$, $SH_x$ or a branched or linear alkyl chain; phenyl-$R_5$—$R_6$—$R_7$ wherein phenyl is a six carbon benzyl ring or a hydrogenated, hydroxylated or halogenated six carbon ring; $R_5$ is $CH_x$, CO, $NH_x$, $OH_x$ or $SH_x$; $R_6$ is $CH_x$, CO, $H_x$, $NH_x$, $OH_x$, $SH_x$ or a branched or linear alkyl chain; $R_7$ is $CH_x$, $H_x$, $NH_x$, $OH_x$, $SH_x$, CO, $CONH_x$, COOH, $COSH_x$, $COOR_8$, $COR_8$ or $OR_8$; $R_8$ is $CH_x$, CO, $H_x$, $NH_x$, $OH_x$, $SH_x$ or a branched or linear aryl chain; and phenyl-$R_9$—$R_{10}$ wherein $R_9$ is $CH_x$, CO, $NH_x$, $OH_x$, $SH_x$, or a branched or linear aryl chain; $R_{10}$ is $CH_x$, CO, $H_x$, $NH_x$, $OH_M$, $SH_x$, $CONH_x$, COOH, $COSH_x$, $COOR_{11}$, $COR_{11}$, CO or $OR_{11}$; and $R_{11}$ is $CH_x$, CO, $H_x$, $NH_x$, $OH_x$, $SH_x$ or a branched or linear alkyl chain; wherein x is 0, 1, 2 or 3. Preferably, $R_4$ comprises between 1 to 8 carbon atoms and more preferably 1, 2, 3 or 4 carbon atoms. Preferably, $R_6$ comprises between 1 to 8 carbon atoms and more preferably 1, 2, 3 or 4 carbon atoms. Preferably, $R_8$ comprises between 1 to 8 carbon atoms and more preferably 1, 2, 3 or 4 carbon atoms.

Examples of chemical compounds of the structure $R_1$—$R_2$—$R_3$ or $R_1$—C(O)—$R_2$—$R_3$ include acids, amines, monoamides and diamides of butyric acid ($H_3C$—$CH_2$—$CH_2$—COOH), butyric acid ethyl ester ($CH_3CH_2CH_2COCH_2CH$), 4,4,4-tri fluorobutyric acid ($CF_3CH_2CH_2COOH$), 2,2-dimethyl butyric acid ($C_2H_5C(CH_3)_2CO_2H$), 2,2-diethyl butyric acid, 3,3-dimethyl butyric acid ($C_6H_{12}O_2$), 3,3-diethyl butyric acid, fumaric acid (HOOCCH=CHCOOH), fumaric acid monomethyl and monoethyl ester, fumaric acid monoamide ($C_4H_5O_2N$), fumaramide ($H_2NCOCHCHCONH_2$), succinic acid ($HOOCCH_2CH_2COOH$) (succinamic acid and succinamide), 2,3-dimethyl succinic acid and methoxy acetic acid ($CH_3CH_2OCH_3$).

Examples of chemical compounds of the structure phenyl-$R_5$—$R_6$—$R_7$ include acids, amines and amides of phenoxyacetic acid ($C_6H_5OCH_2COOH$; $C_6H_5$ $OCH_2COONH_3$), 2- and 3-thiophenoxy propionic acid ($C_6H_5SCH(CH_3)COOH$; $C_6H_5$ $SCH_2CH_2COOH$), 2- and 3-phenoxy propionic acid ($C_6H_5OCH(CH_3)COOH$; $C_6H_5OCH_2$ $CH_2COOH$), 2- and 3-phenyl propionic acid ($C_6H_5CH(CH_3)COOH$; $C_6H_5CH_2CH_2$ COOH), 4-chlorophenoxy-2-propionic acid ($ClC_6OCH_2CH_2CO_2H$), methoxy acetic acid ($H_3COCH_2CO_2H$), and 2-thiophenoxy acetic acid ($C_6H_5SCH_2COOH$).

Examples of chemical compounds of the structure phenyl-$R_9$—$R_{10}$ include acids, amines and amides of cinnamic acid ($C_6H_5CH$=CHCOOH), hydrocinnamic acid, dihydrocinnamic acid ($C_6H_5CH_2CH_2COOH$), a-methyl hydrocinnamic acid or dihydro cinnamic acid, 2,3-dimethyl hydrocinnamic or dihydrocinnamic acid, phenyl acetate ethyl ester ($C_6H_5CH(CH_3)CH_2COCH_2CH_3$), 2-phenoxypropionic acid ($C_6H_5OCH_2$ $CO_2H$), phenoxy acetic acid ($CH_3CH(OC_6H_5)CO_2H$), and 3-phenyl butyric acid ($C_6H_5CH$ $(CH_3)CH_2COOH$). Additional chemical compounds which may or may not be included in the above classification scheme include monobutyrin, tributyrin ($CH_2(OCOCH_2$ $CH_2CH_3)$ $CH(OCOCH_2CH_2CH_3)CH2(OCOCH_2CH_2CH_3)$), ethyl-phenyl acetic acid ($CH_3$ $CH_2C_6H_5CH_2COOH$), indol-3-propionic acid, indol-3-butyric acid, 1- and 2-methyl cyclopropane carboxylic acid ($C_5H_8O_2$ and $C_6H_8O_2$), mercaptoacetic acid ($C_2H_4O_2S$), N-acetylglycine ($C_4H_7O_3N$), squaric acid ($C_4H_2O_4$), 4-trifluorobutanol ($C_4H_7OF_3$), chloropropionic acid ($ClCH_2CH_2CO_2H$), 3-trimethyl silyl-1-proposulfonic acid sodium ($C_6H_{15}O_3SS$), 2-oxopantansane ($C_5H_8O_3$), isobutyl hydroxylamine HCl ($C_4H_{12}OCl$), 2-methyl butanoic acid ($C_5H_{10}O_2$), o-benzoyl lactate, n-dimethyl-butyric acid glycine amide, o-dimethyl butyric acid lactate, and diethyl butyric acid.

Agents are useful in pharmaceutical compositions for the treatment of cystic fibrosis. Preferred agents in such compositions include, for example, propionic acid, butyric acid, succinic acid, fumaric acid monoethyl ester, dimethyl butyric acid, trifluorobutanol ($C_4H_7OF_3$), chloropropionic acid ($ClCH_2CH_2COOH$), isopropionic acid, 2-oxypentasane ($CH_3CH_2CH_2C(O)COOH$), 2,2- or 3,3-dimethyl butyric acid ($C_6H_{12}O_2$), 2,2- or 3,3-diethyl butyric acid ($C_8H_{16}O_2$), butyric acid ethyl ester, 2-methyl butanoic acid ($C_5H_{10}O_2$), fumaric acid ($C_4H_4O_3$) and amides and salts thereof. Other examples include methoxy acetic acid ($H_3C(O)CH_2COOH$), dimethyl butyric acid, methoxy propionic acid, N-acetylglycine ($H_3CC(O)NCH_2COOH$), mercaptoacetic acid ($HSCH_2COOH$), 1- or 2-methyl cyclopropane carboxylic acid ($C_5H_8O_2$), squaric acid ($C_4H_2O_4$), 2- or 3-phenoxy propionic acid, methoxy butyric acid, phenoxy acetic acid, 4-chloro-2-phenoxy 2-propionic acid, 2- or 3-phenoxy butyric acid, phenyl acetic acid, phenyl propionic acid, 3-phenyl butyric acid, ethyl-phenyl acetic acid, 4-chloro-2-phenoxy-2-propionic acid, n-dimethyl butyric acid glycine amide, o-benzoyl lactic acid, o-dimethyl butyric acid lactate, cinnamic acid, dihydrocinnamic acid ($C_6H_5CHCH_3$ COOH), a-methyl-dihydrocinnamic acid, thiophenoxy acetic acid, and amines, amides and salts of these chemicals.

Useful amines and amides include isobutylhydroxylamine: HCl ($C_4H_{12}$ OCl), fumaric acid monoamide ($C_4H_5O_2N$), fumaramide ($H_2NCOCHCHCONH_2$), succinamide and isobutyramide ($C_4H_9ON$). Salts can be sodium, potassium, calcium, ammonium, lithium or choline such as sodium 3-trimethyl silyl-1-proposulfonic acid ($C_6H_{15}O_3SiS$:Na). Reagents which may be electrostatically or covalently bonded with the inducing agent include amino acids such as arginine (arginine butyrate), glycine, alanine, asparagine, glutamine, histidine or lysine, nucleic acids including nucleosides or nucleotides, or substituents such as carbohydrates, saccharides, lipids, fatty acids, proteins or protein fragments. Combinations of these salts with the inducing agent can also produce useful new compounds from the interaction of the combination.

Chemical compounds are preferably optically pure with a specific conformation (plus {+} or minus {−}), absolute configuration (R or S), or relative configuration (D or L). Particular salts such as sodium, potassium, magnesium, calcium, choline, amino acid, ammonium or lithium, or combinations of salts may also be preferred, however, certain salts may be more advantageous than others. For example, chemical compositions that require high doses may introduce too much of a single salt to the patient. Sodium is generally an undesirable salt because at high doses, sodium can increase fluid retention resulting in tissue destruction. In such instances, lower doses or combinations of different or alternative salts can be used. For example, compounds of the invention may be substituted with one or more halogens such as chlorine (Cl), fluorine (F), iodine (I), bromine (Br) or combinations of these halogens. As known to those of ordinary skill in the art, halogenation can increase the polarity, hydrophilicity or lipophilicity or a chemical compound which can be a desirable feature, for example, to transform a chemical compound into a composition which is more easily tolerated by the patient or more readily absorbed by the epithelial lining of the gastrointestinal tract. Such compositions could be orally administered to patients.

Therapeutically effective chemical compounds may be created by modifying any of the above chemical compounds so that after introduction into the patient, these compounds metabolize into active forms, such as the forms above, which have the desired effect on the patient. Compounds may also be created which are metabolized in a timed-release fashion allowing for a minimal number of introductions which are efficacious for longer periods of time. Combinations of chemical compounds can also produce useful new compounds from the interaction of the combination. Such compounds may also produce a synergistic effect when used in combination with other known or other compounds.

Compositions are preferably physiologically stable at therapeutically effective concentrations. Physiological stable compounds are compounds that do not break down or otherwise become ineffective upon introduction to a patient prior to having a desired effect. Compounds are structurally resistant to catabolism, and thus, physiologically stable, or coupled by electrostatic or covalent bonds to specific reagents to increase physiological stability. Such reagents include ammo acids such as arginine, glycine, alanine, asparagine, glutamine, histidine or lysine, nucleic acids including nucleosides or nucleotides, or substituents such as carbohydrates, saccharides and polysaccharides, lipids, fatty acids, proteins, or protein fragments. Useful coupling partners include, for example, glycol such as polyethylene glycol, glucose, glycerol, glycerin and other related substances.

Physiological stability can be measured from a number of parameters such as the half-life of the compound or the half-life of active metabolic products derived from the compound. Certain compounds of the invention have in vivo half lives of greater than about fifteen minutes, preferably greater than about one hour, more preferably greater than about two hours, and even more preferably greater than about four hours, eight hours, twelve hours or longer. Although a compound is stable using this criteria, physiological stability cam also be measured by observing the duration of biological effects on the patient. Clinical symptoms which are important from the patient's perspective include a reduced frequency or duration, or elimination of the need for oxygen, inhaled medicines, or pulmonary therapy. Preferably, a stable compound of the invention has an in vivo half-life of greater than about 15 minutes, a serum half-life of greater than about 15 minutes, or a biological effect which continues for greater than 15 minutes after treatment has been terminated or the serum level of the compound has decreased by more than half.

Preferably, compositions are also not significantly biotransformed, degraded or excreted by catabolic processes associated with metabolism. Although there may be some biotransformation, degradation or excretion, these functions are not significant if the composition is able to exert its desired effect.

Compositions are also preferably safe at effective dosages. Safe compositions are compositions that are not substantially toxic (e.g. cytotoxic or myelotoxic), or mutagenic at required dosages, do not cause adverse reactions or side effects, and are well-tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures and other central nervous system difficulties, fever, bleeding or hemorrhaging, serum abnormalities and respiratory difficulties.

Compositions useful for treating disorders preferably do not substantially affect the viability of a cell such as a normal mammalian cell, the cell being treated or effected by the chemical compound. Normal cell viability, the viability of an untransformed or uninfected cell, can be determined from analyzing the effects of the composition on one or more biological processes of the cell. Detrimental interference with one or more of these cellular processes becomes significant when the process becomes abnormal. Examples of quantitatable and qualifiable biological processes include the processes of cell division, protein synthesis, nucleic acid (DNA or RNA) synthesis, nucleic acid (principally DNA) fragmentation and apoptosis. Others processes include specific enzyme activities, the activities of the cellular transportation systems such as the transportation of amino acids by system A (neutral), system B (acidic) or system C (basic), and the expression of a cell surface protein. Each of these parameters is easily determined as significantly detrimental, for example, in tissue culture experiments, in animal experiments or in clinical studies using techniques known to those of ordinary skill in the art. Abnormal cell division, for example, can be mitosis which occurs too rapidly, as in a malignancy, or unstably, resulting in programmed cell death or apoptosis, detected by increased DNA degradation. The determination of abnormal cell viability can be made on comparison with untreated control cells. Compositions preferably increase normal cell viability. Increased cell viability can be determined by those of ordinary skill in the art using, for example, DNA fragmentation analysis. A decreased amount of fragmentation indicates that cellular viability is boosted. Determinations of increased or decreased viability can also be concluded from an analysis of the results of multiple different assays. Where multiple tests provide conflicting results, accurate conclusions can still be drawn by those of ordinary skill based upon the cell type, the correctness or correlation of the tests with actual conditions and the type of composition.

Compositions can be prepared in solution as a dispersion, mixture, liquid, spray, capsule or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil or a relatively inert solid or liquid. Liquids, pills, capsules or tablets administered orally may also include flavoring agents to increase palatability. Additionally, all compositions may further comprise agents to increase shelf-life, such as preservatives, antioxidants and other components necessary and suitable for manufacture and distribution of the composition. Compositions further comprise a pharmaceutically acceptable carrier. Carriers are chemical or multi-chemical compounds that do not significantly alter or effect the active ingredients of the compositions. Examples include water, alcohols such as glycerol and polyethylene glycol, glycerin, oils, salts such as sodium, potassium, magnesium and ammonium, fatty acids, saccharides or polysaccharides. Carriers may be single substances or chemical or physical combinations of these substances.

Another embodiment of the invention is directed to combinations of compositions comprising a chemical compound in combination with an agent known to positively affect expression of the CFTR molecule. The agent may be a chemical compound such as glycerol, acetic acid, butyric acid, D- or L-amino-n-butyric acid, alpha- or beta-amino-n-butyric acid, arginine butyrate or isobutyramide, all disclosed in U.S. Pat.

Nos. 4,822,821 and 5,025,029. Others include butyrin, 4-phenyl butyrate ($C_6H_5CH_2CH_2CH_2COOH$), phenylacetate ($C_6H_5CH_2COOH$), phenoxy acetic acid, all of which and more are disclosed in U.S. Pat. No. 4,704,402, and U.S. patent application Ser. No. 08/398,588 (entitled "Compositions for the Treatment of Blood Disorders" filed Mar. 3, 1995), and derivatives, salts and combination of these agents. The agent may be a protein such as hsp70 or a growth factor or cytokine. The agent may be a gene or a nucleotide sequence. Such composition may have additive or synergistic effects.

In another embodiment, compositions of the invention may contain one or more chemical compounds that increase the extent or magnitude of CFTR function, increase the expression of the CFTR molecule, increase transport of the CFTR molecule to the cell surface, increase the half-life (physical stability or thermal stability) of the molecule, increase expression from the CFTR gene, increase CFTR transcript levels, or increase post-transcriptional processes which increase the levels of CFTR transcript, or increase translation or enhance post-translational processing of the CFTR gene product. Stimulation of specific gene expression involves activation of transcription or translation promoters or enhancers, or alteration of the methylation patterns or histone distribution along the gene to promote expression. Expression may also be stimulated by inhibition of specific transcriptional or translational repressors, activation of specific transcriptional or translational activation factors, or activation of receptors on the surface of particular populations of cells. Stimulation may recruit additional epithelial cells to the airways, reprogram differentiated epithelial cells to express CFTR. Stimulation may also activate a previously dormant or relatively inactive gene.

Compositions of the invention may be administered by oral, parenteral, sublingual, rectal or enteral administration, or pulmonary absorption or topical application. Compositions cam be directly or indirectly administered to the patient. Indirect administration is performed, for example, by administering the composition to cells ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Direct administration of a composition may be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intraperitoneal injection or direct injection or other administration to the desired site. Injectable forms of administration are sometimes preferred for maximal effect. When long term administration by injection is necessary medi-ports, in-dwelling catheters, or automatic pumping mechanisms are also preferred wherein direct and immediate access is provided to the arteries in and around the heart and other major organs and organ systems.

An effective method of administration to a specific site may be by transdermal transfusion such as with a transdermal patch, by direct contact to the cells or tissue, if accessible, such as a skin tumor, or by administration to an internal site through an incisions or some other artificial opening into the body. Compositions may also be administered to the nasal passages as a spray. Diseases localized to the head and brain area are treatable in this fashion as arteries of the nasal area provide a rapid and efficient access to the upper areas of the head. Sprays also provide immediate access to the pulmonary system and are the preferable methods for administering compositions to these areas. Access to the gastrointestinal tract is gained using oral, enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months.

Orally active compositions are preferred, as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or modifying the compound with a neutralizing chemical group. Oral bioavailability is also a problem because drugs are exposed to the extremes of gastric pH and gastric enzymes. These problems can be overcome in a similar matter by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

Compounds may also be used in combination with other agents to maximize the effect of the compositions in an additive or synergistic manner. Cytokines which may be effective in combination with the compositions of the invention include growth factors such as B cell growth factor (BCGF), fibroblast-derived growth factor (FGF), granulocyte/macrophage colony stimulating factor (GM-CSF), granulocyte colony stimulating factor (G-CSF), macrophage colony stimulating factor (M-CSF), epidermal growth factor (EGF), vascular endothelial growth factor (VEGF), platelet derived growth factor (PDGF) nerve growth factor (NGF), stem cell factor (SCF), and transforming growth factor (TGF). These growth factors plus a composition may further stimulate cellular differentiation and/or the expression of the CFTR molecule or function.

Alternatively, other cytokines and related antigens in combination with a composition may also be useful to treat cystic fibrosis. Potentially useful cytokines include tumor necrosis factor (TNF), the interleukins IL-I, IL-2, IL-3, IL-4, IL-5, IL-6, etc., recombinant IL receptors, growth factors, colony stimulating factors, erythropoietin (EPO), the interferon (IFN) proteins IFN-alpha, IFN-beta, and IFN-gamma; cyclic AMP including dibutyryl cyclic AMP, hemin, DMSO, hydroxyurea, hypoxanthine, glucocorticoid hormones and cytosine arabinoside. Therapies using combinations of these agents would be safe and effective therapies cystic fibrosis. Combinations of therapies may also be effective in inducing improvement of the symptoms of cystic fibrosis such as compositions of the invention plus the reintroduction of a normal or altered CFTR gene (gene therapy), toxin or drug conjugated antibody therapy using monoclonal or polyclonal antibodies directed against the pulmonary cells, or specific antisense therapy. Effects may be additive, logarithmic or synergistic, and methods involving combinations of therapies may be simultaneous protocols, intermittent protocols or protocols which are empirically determined.

Another embodiment of the invention is directed to the pulsed administration of pharmaceutical compositions for the treatment or prevention of cystic fibrosis. Pulsed administration is surprisingly more effective than continuous treatment as pulsed doses are often lower than would be expected from continuous administration of the same composition. Each pulse dose can be reduced and the total amount of drug administered over the course of treatment to the patient is minimized.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient drug available for a long period of time. Pulsed administration can substantially reduce the amount of the composition administered to the patient per dose or per total treatment regimen with an increased effectiveness. This represents a significant saving in time, effort and expense and, more importantly, a lower effective dose substantially lessens the number and severity of complications that may be experienced by the patients. As such, pulsing is surprisingly more effective than continuous administration of the same composition.

Preferably, compositions contain chemicals that are substantially non-toxic. Substantially non-toxic means that the composition, although possibly possessing some degree of toxicity, is not harmful to the long-term health of the patient. Although the active component of the composition may not be toxic at required levels, there may also be problems associated with administering the necessary volume or amount of the final form of the composition to the patient. For example, if the composition contains a salt, although the active ingredient may be at a concentration that is safe and effective, there can be a harmful build-up of sodium, potassium or another ion. With a reduced requirement for the composition or at least the active component of that composition, the likelihood of such problems can be reduced or even eliminated. Consequently, although patients may have minor or short term detrimental side-effects, the advantages of taking the composition outweigh the negative consequences.

Compositions most effective at pulsed administration are typically non-toxic or non-cytotoxic chemicals without any substantial proteinaceous active component at the therapeutically effective pulsed dose. Preferably, treatment does not stimulate apoptosis in the cells being directly treated or in the otherwise normal cells of the body which will also be exposed to the composition.

Individual pulses can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours. Alternatively, periodic doses can be administered in a single bolus or a small number of injections of the composition over a short period of time, typically less than 1 or 2 hours. For example, arginine butyrate has been administered over a period of 4 days with infusions for about 8 hours per day or overnight, followed by a period of 7 days of no treatment. The interval between pulses or the interval of no delivery is greater than 24 hours and preferably greater than 48 hours, and can be for even longer such as for 3, 4, 5, 6, 7, 8, 9 or 10 days, two, three or four weeks or even longer. As the results achieved may be surprising, the interval between pulses, when necessary, can be determined by one of ordinary skill in the art. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life. For compositions with fairly rapid half lives such as arginine butyrate with a half-life of 15 minutes, intervals may be 25, 50, 100, 150, 200, 250 300 and even 500 times the half life of the chemical composition.

The number of pulses in a single therapeutic regimen may be as little as two, but is typically from about 5 to 10, 10 to 20, 15 to 30 or more. In fact, patients can receive drugs for life according to the methods of this invention without the problems and inconveniences associated with current therapies. Compositions can be administered by most any means, but are preferably delivered to the patient as an injection (e g intravenous, subcutaneous, intraarterial), infusion or instillation, and more preferably by oral ingestion. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Compositions administered in pulses have the surprising benefit of reducing the overall load of drug on the patient as the total amount of drug administered can be substantially less than that amount that has been therapeutically administered by conventional continuous therapy. Substantially means that there is more than an insignificant difference between the amount or concentration of a composition administered by pulsing according to the invention verses the amount or concentration administered using conventional therapy, without compromising the beneficial effect achieved to the patient. For example, arginine butyrate has been shown to be effective at continuous administration at about 2000 mg/kg patient weight. Doses of between about 400 to 1500 mg/kg, preferably from about 600 to 1000 mg/kg and more preferably from 700 to 800 mg/kg, when administered in pulses, are surprisingly more beneficial as measured by a rise in fetal hemoglobin levels in thalassemic patients. Typical pulsed amounts of arginine butyrate are from about 2 to about 20 g/kg/month, and preferably from about 3 to about 10 g/kg/month wherein the patient receives a total of less than about 20 kg per month, preferably less than about 15 kg per month and more preferably less than about 10 kg per month. The amounts administered per pulse as well as the total amount of the composition received by the patient over the regimen is substantially reduced. Preferably, the therapeutically effective pulsed dose is less than the continuous dose, or less than one half, one third, one quarter, one fifth, one tenth or even one twentieth of the therapeutic continuous dose of the same composition or even less.

Other embodiments and uses of the invention will be apparent to those skilled in the art from consideration of the specification and practice of the invention disclosed herein. All U.S. patents and patent applications, including provisional applications, and all other documents referenced herein, for whatever reason, are specifically incorporated by reference. It is intended that the specification and examples be considered exemplary only, with the true scope and spirit of the invention being indicated by the following claims.

We claim:

1. An oral pharmaceutical composition comprising a pharmaceutically effective amount of 2,2-dimethylbutyric acid, or a pharmaceutically acceptable salt thereof; and a pharmaceutically acceptable carrier;

wherein the pharmaceutical composition is for oral administration; and wherein the 2,2-dimethylbutyric acid has an in vivo half-life of greater than about 15 minutes.

2. The oral pharmaceutical composition of claim 1, wherein the pharmaceutical composition comprises a pharmaceutically effective amount of the sodium salt of 2,2-dimethylbutyric acid.

3. The oral pharmaceutical composition of claim 1, wherein the oral pharmaceutical composition is in the form of a liquid, pill, capsule or tablet.

4. The oral pharmaceutical composition of claim 3, wherein the oral pharmaceutical composition is in the form of a capsule.

5. The oral pharmaceutical composition of claim 3, wherein the oral pharmaceutical composition is in the form of a tablet.

* * * * *